United States Patent
Rosenfeld et al.

(10) Patent No.: US 9,340,823 B2
(45) Date of Patent: May 17, 2016

(54) GENE EXPRESSION SIGNATURE FOR CLASSIFICATION OF KIDNEY TUMORS

(71) Applicants: Rosetta Genomics Ltd., Rehovot (IL); Tel Hashomer Medical Research Infrastructure and Services Ltd., Ramat Gan (IL)

(72) Inventors: Nitzan Rosenfeld, Rehovot (IL); Yael Spector, Tel Aviv (IL); Eddie Friedman, Kfar-Sava (IL); Zohar Dotan, Hod Hasharon (IL)

(73) Assignees: Rosetta Genomics, Ltd., Rehovot (IL); Tel Hashomer Medical Research Infrastructure and Services Ltd., Ramat Gan (IL)

( * ) Notice: Subject to any disclaimer, the term of this patent is extended or adjusted under 35 U.S.C. 154(b) by 0 days.

(21) Appl. No.: 14/168,981

(22) Filed: Jan. 30, 2014

(65) Prior Publication Data

US 2014/0243230 A1    Aug. 28, 2014

Related U.S. Application Data

(62) Division of application No. 13/057,750, filed as application No. PCT/IL2009/000765 on Aug. 5, 2009, now abandoned.

(60) Provisional application No. 61/086,483, filed on Aug. 6, 2008, provisional application No. 61/158,368, filed on Mar. 8, 2009.

(51) Int. Cl.
C12Q 1/68    (2006.01)

(52) U.S. Cl.
CPC ............... *C12Q 1/68* (2013.01); *C12Q 1/6886* (2013.01); *C12Q 2600/112* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2005/0107325 A1 | 5/2005 | Manoharan et al. |
| 2005/0182005 A1 | 8/2005 | Tuschl et al. |
| 2006/0183120 A1* | 8/2006 | Teh et al. ............... 435/6 |
| 2006/0292617 A1 | 12/2006 | Neely et al. |
| 2007/0065844 A1 | 3/2007 | Golub et al. |
| 2007/0092882 A1 | 4/2007 | Wang et al. |
| 2008/0182239 A1 | 7/2008 | Mullinax et al. |

FOREIGN PATENT DOCUMENTS

| | | | |
|---|---|---|---|
| WO | WO-2004/032842 A2 | | 4/2004 |
| WO | WO 2007148235 A2 * | | 12/2007 |

OTHER PUBLICATIONS

Griffiths-Jones et al. miRBase: tools for microRNA genoomics. Nucleic Acids Research, vol. 36, pp. D154-D158, 2008, published online Nov. 8, 2007.*
Akobeng, AK, "Understanding diagnostic tests 3: receiver operating characteristic curves," Acta Paediatrica, 2007, pp. 644-647, vol. 96.
Allory et al. "Profiling and classification tree applied to renal epithelial tumors," Histopathology, 2008, pp. 158-166, vol. 52.
Bartel et al., "MicroRNAs: At the Root of Plant Development?," Plant Physiology, Jun. 2003, pp. 709-717, vol. 132.
Bartel et al., "MicroRNAs: Genomics, Biogenesis, Mechanism, and Function," Cell., Jan. 2004, pp. 281-297, vol. 116.
Brennecke et al., "Principles of MicroRNA-Target Recognition," PLos Biology, Mar. 2005, pp. 404-418, vol. 3, No. 3, e85.
Calin et al., "MicroRNA profiling reveals distinct signatures in B cell chronic lymphocytic leukemias," Proceedings of the National Academy of Sciences of USA, Aug. 2004, pp. 11755-11760, vol. 101.
Chen et al., "Messenger RNA expression ratios among four genes predict subtypes of renal cell carcinoma and distinguish oncocytoma from carcinoma," Clinical Cancer Research, Sep. 2005, pp. 6558-6566, vol. 11, No. 18.
Chen et al., "Real-time quantification of microRNAs by stem-loop RT-PCR," Nucleic Acids Research, Nov. 2005, printed as pp. 1/9 to 9/9, p. e179, vol. 33, No. 20.
Golub et al., "Molecular classification of cancer: Class discovery and class prediction by gene expression monitoring," Science, Oct. 1999, pp. 531-537, vol. 286.
Gottardo et al. Micro-RNA profiling in kidney and bladder cancers, Urologic Oncology, Sep. 2007, pp. 387-392, vol. 25, No. 5.
Higgins et al., "Gene expression patterns in renal cell carcinoma assessed by complementary DNA microarray," American Journal of Pathology, Mar. 2003, pp. 925-932, vol. 162, No. 3.
Hillig et al., "Identification of A miRNA Signature in Renal Cell Cancer," Journal of Urology, May 2008, p. 92, vol. 179, No. 4.
International Search Report mailed Dec. 3, 2009 in PCT/IL2009/000765.
Jemal et al., "Cancer Statics, 2008," CA Cancer J Clin, Mar./Apr. 2008, pp. 71-96, vol. 58, No. 2.
Juan et al., "MicroRNA Expression Profile in Clear-Cell Kidney Cancer," Journal of Urology, May 2008, p. 92, vol. 179, No. 4.
Krek et al., "Combinational microRNA target predictions," Nature Genetics, May 2005, pp. 495-500.
Krutzfeldt et al., "Silencing of microRNAs in vivo with 'antagomers,'" Nature, 2005, pp. 1-5.
Landgraf et al., "A mammalian microRNA expression atlas based on small RNA library sequencing," Cell, Jun. 29, 2007, pp. 1401-1414, vol. 129, including the entry for hsa-miR-455 of Table S12.
Lewis et al., "Conserved Seed Pairing, Often Flanked by Adenosines, Indicates that Thousands of Human Genes are MicroRNA Targets," Cell, Jan. 2005, pp. 15-20, vol. 120.

(Continued)

*Primary Examiner* — Jennifer Dunston
(74) *Attorney, Agent, or Firm* — Polsinelli PC; Ron Galant

(57) ABSTRACT

The present invention provides a method for classification of kidney tumors through the analysis of the expression patterns of specific microRNAs and nucleic acid molecules relating thereto. Classification according to a microRNA expression framework allows optimization of treatment, and determination of specific therapy.

6 Claims, 11 Drawing Sheets

(56) References Cited

OTHER PUBLICATIONS

Lopez-Beltran et al., "Targeted therapies and biological modifiers in urologic tumors: pathology and clinical implications," Seminars in Diagnostic Pathology, Nov. 2008, pp. 232-244., vol. 130.

Lu et al., MicroRNA expression profiles classify human cancers, Nature, Jun. 2005, pp. 834-838, vol. 435, No. 7043.

Lui et al., "Patterns of known and novel small RNAs in human cervical cancer," Cancer Research, Jul. 6, 2007, pp. 6031-6043, vol. 67.

Ma et al., "Molecular Classification of Human Cancers Using a 92-Gene Real-Time Quantitative Polymerase Chain Reaction Assay," Arch Pathol Lab Med, Apr. 2006, pp. 465-473, vol. 130.

miRNA entry for M10003513, printed from http://www/mirbase.org/cgi-bin/mirna_entry.pl?acc=MIOOO3513 as pp. 1/4 to 4/4 on Dec. 20, 2012.

Pusztai and Hess, "Clinical trial design for microarray predictive marker discovery and assessment," Annals of Oncology, 2004, pp. 1731-1737, vol. 15.

Rosenfeld et al., "MicroRNAs accurately identify cancer tissue origin," Nature Biotechnology, Apr. 2008, pp. 462-469, vol. 26, No. 4.

Shannon et al., "The Value of Preoperative Needle Core Biopsy for Diagnosing Benign Lesions Among Small, Incidentally Detected Renal Masses," J Urology, Oct. 2008, pp. 1257-1261, vol. 180.

Shi et al. "Facile means for quantifying microRNA expression by real-time PCR," BioTechniques, Oct. 2005, pp. 519-524, vol. 39, No. 4.

Singer et al., "Targeted therapies for non-clear renal cell carcinoma," Targeted Oncology, Jun. 2010, pp. 119-129, vol. 5, No. 2.

Soutschek et al., "Therapeutic silencing of an endogenous gene by systemic administration of modified siRNAs," Nature, Nov. 2004, pp. 173-178, vol. 432.

Spector et al., "Development and validation of a microRNA-based diagnostic assay for classification of renal cell carcinomas," Molecular Oncology, Mar. 2013, pp. 732-738, vol. 7.

Sun et al., "Development of a micro-array to detect human and mouse microRNAs and characterization of expression in human organs," Nucleic Acids Research, 2004, p. E188, vol. 32, No. 22.

Tazi et al., "Advanced treatments in non-clear renal cell carcinoma," Urology Journal, Winter 2011, pp. 1-11, vol. 8, No. 1.

Yekta et al., "MicroRNA-Directed Cleavage of HOXB8 mRNA," Science, Apr. 2004, pp. 594-596, vol. 304.

* cited by examiner

GENE EXPRESSION SIGNATURE FOR CLASSIFICATION OF KIDNEY TUMORS

CROSS REFERENCE TO RELATED APPLICATIONS

The present application is a divisional of U.S. patent application Ser. No. 13/057,750, filed on Feb. 4, 2011, which is the national stage of International Application No. PCT/IL2009/000765, filed on Aug. 5, 2009. International Application No. PCT/IL2009/000765 claims priority to U.S. Provisional Application No. 61/086,483, filed Aug. 6, 2008 and U.S. Provisional Application No. 61/158,368, filed Mar. 8, 2009 which are herein incorporated by reference in their entirety.

FIELD OF THE INVENTION

The present invention relates to methods for classification of kidney tumors. Specifically the invention relates to microRNA molecules associated with specific kidney tumors, as well as various nucleic acid molecules relating thereto or derived therefrom.

BACKGROUND OF THE INVENTION

In recent years, microRNAs (miRs) have emerged as an important novel class of regulatory RNA, which have a profound impact on a wide array of biological processes. These small (typically 18-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. The expression of many miRs was found to be altered in numerous types of human cancer, and in some cases strong evidence has been put forward in support of the conjecture that such alterations may play a causative role in tumor progression. The remarkable tissue-specificity of miR expression allows the development of novel approaches to molecular classification. There are currently about 885 known human miRs.

Renal cancers account for more then 3% of adult malignancies and cause more than 13,000 deaths per year in the US alone (Jemal, A., et al. 2008, Cancer statistics, CA Cancer J Clin 58, 71-96). The incidence of renal cancers in the US rose more then 50% between 1983 to 2002 and the estimated number of new cases per year rose from 39,000 estimated in 2006 to 54,000 estimated in 2008. Despite the trend of increased incidence of relatively small and kidney-confined disease, the rate of mortality has not changed significantly during the last 2 decades in the U.S. and Europe. In the 1980s, renal tumors were basically regarded as one disease: the higher the stage and the grade, the worse is the prognosis. After the 1980s, molecular biologists and pathologists described new entities with different morphological and biological characteristics. Evidence for different long-term prognosis for these subtypes makes the correct pathological diagnosis of a renal cancer critically important for the clinician. Currently, it is well accepted that renal cell carcinoma (RCC) is a family of carcinomas which arise from the epithelium of the renal tubules. The current classification of renal cell carcinoma includes four main types: conventional cell (also known as clear cell), papillary, chromophobe, and collecting duct carcinoma, as well as unclassified renal cell carcinoma. Oncocytoma is a benign subtype of RCC.

Conventional cell renal carcinoma is the most frequent subtype of RCC and accounts for 60-70% of cases and account for the majority of renal cell cancer specific mortality. The term "conventional cell" is used to replace the name "clear cell", because some types have eosinophilic cytoplasm, generating a more difficult diagnostic challenge. In tumors of this type, a characteristic vascular network is commonly observed. The conventional cell carcinoma type is associated with germ line and somatic mutations of the von Hippel-Lindau (VHL) suppressor gene, and such mutations may indicate a more favorable prognosis. Papillary RCC typically consists of a central fibrovascular core with epithelial covered papillae. It is subclassified into type 1 and 2 tumors that differ in terms of morphology, genotype and clinical outcome. Genetically, this type of tumor is associated with polysomies of chromosomes 7 or 17 and deficiency of Y. Chromophobe renal cell carcinoma was included before 1986 in the group of conventional cell RCC. The typical form exhibits balloon cells with an abundant granular pale cytoplasm, or eosinophilic cytoplasm that resemble the cells of oncocytoma. Such features as described above are characteristic of the histological subtypes, but inter-observer variations limit the accuracy of histological classification, with some types identified with a sensitivity of 70% or lower. Furthermore, underlying biological mechanisms playing important roles in these tumors are yet to be elucidated.

These different histological subtypes of RCC vary in their clinical courses and their prognosis, and different clinical strategies have been developed for their management. Patients with conventional cell renal carcinoma have a poorer prognosis, and differences may also exist between the prognosis of patients with papillary or chromophobe RCC. The histological types arise through different constellations of genetic alterations, and show expression or mutation in different oncogenic pathways; they therefore offer different molecular candidates for targeted therapy (e.g., mTOR, VEGF, KIT). Initial studies show differences in the responses of RCC subtypes to targeted therapies (Lopez-Beltran, A., et al. 2008, Semin Diagn Pathol 25, 232-44), and future therapies are likely to be individualized for the different types. The correct identification of these subtypes is therefore important choice of treatment, and for the selection of patients for clinical trials.

Based on the growing clinical demand for accurate diagnosis of RCC subtypes, recent studies focused on the immunohistochemical profiling of different carcinomas. Allory et al lately described a subset of 12 antibodies as base for classification of renal cell carcinomas. In this report AMACR, CK7 and CD10 had the most powerful classification trees with 78%-87% of carcinomas correctly classified (Allory, Y., et al. 2008, Histopathology 52, 158-66) Immunohistochemistry provides limited information for distinguishing chromophobe RCC from oncocytoma. However, the increasing number of smaller tumors and needle-biopsy procedures places a strain on immunohistochemical methods. In a recent large study of 235 cases, more than 20% of the core needle biopsies were nondiagnostic (Shannon, B. A., et al. 2008, J Urol 180, 1257-61). This emphasized the need for developing additional types of molecular markers for the classification of renal tumors and for their study.

SUMMARY OF THE INVENTION

The present invention provides nucleic acid sequences for use in the identification, classification and diagnosis of particular subtypes of kidney tumors. The nucleic acid sequences can also be used as prognostic markers for prognostic evaluation and determination of appropriate treatment of a subject based on the abundance of the nucleic acid sequences in a biological sample.

The present invention further provides a method of classifying kidney tumors, the method comprising: obtaining a biological sample from a subject; determining expression of individual nucleic acids in a predetermined set of microRNAs; and classifying the specific subtype of kidney tumor in said sample.

The present invention is based in part on using microRNA microarrays with a training set of 71 formalin-fixed, paraffin-embedded (FFPE) renal tumor samples, and identifying microRNAs that have specific expression levels in distinct tumor types. Clustering showed a strong similarity between oncocytoma and chromophobe subtypes, and between papillary and conventional-cell tumors. By basing a classification algorithm on this structure, inherent biological correlations were followed, and could achieve accurate classification using few microRNAs markers. A two-step decision-tree classifier was defined that uses expression levels of six microRNAs: the first step uses expression levels of hsa-miR-210 (SEQ ID NO: 20) and hsa-miR-221 (SEQ ID NO: 25) to distinguish between the two pairs of subtypes; the second step uses either hsa-miR-200c (SEQ ID NO: 34) with hsa-miR-139-5p (SEQ ID NO: 14) to identify oncocytoma from chromophobe, or hsa-miR-31 (SEQ ID NO: 4) with hsa-miR-126 (SEQ ID NO: 41) to identify conventional-cell (clear cell) from papillary tumors. Tested on an independent set of 56 samples, this classifier identified correctly 93% of the cases. These results were further validated by quantitative real-time PCR (qRT-PCR).

According to one aspect, the present invention provides a method for the detection of a specific subtype of kidney tumor, the method comprising: obtaining a biological sample from a subject; determining an expression profile in said sample of nucleic acid sequences selected from the group consisting of SEQ ID NOS: 1-75, and a sequence having at least about 80% identity thereto; and comparing said expression profile to a reference value; whereby an altered expression levels of the nucleic acid sequence allows the detection of the specific subtype of kidney tumor in said sample.

According to certain embodiments, the nucleic acid sequences are selected from the group consisting of SEQ ID NOS: 4, 14, 20, 25, 34, 41, and a sequence having at least about 80% identity thereto.

According to certain embodiments, said specific subtype is selected from the group consisting of oncocytoma, clear cell (conventional) RCC, papillary RCC and chromophobe RCC.

According to some embodiments, said altered expression level is a change in a score based on a combination of expression levels of said nucleic acid sequences.

The invention further provides a method for distinguishing between benign and malignant kidney tumor, the method comprising: obtaining a biological sample from a subject; determining in said sample an expression profile of nucleic acid sequences selected from the group consisting of SEQ ID NOS: 1-27, 47, 49, a fragment thereof or a sequence having at least 80% identity thereto; and comparing said expression profile to a reference value; whereby a relative abundance of said nucleic acid sequences allows the detection of said kidney tumor.

According to some embodiments, a relative abundance of nucleic acid sequences selected from the group consisting of SEQ ID NOS: 12-15, 18, 19, 25-27 is indicative of the presence of benign kidney tumor.

According to other embodiments, a relative abundance of nucleic acid sequences selected from the group consisting of SEQ ID NOS: 1-11, 16, 17, 20-24, 47, 49 is indicative of the presence of malignant kidney tumor.

The invention further provides a method for distinguishing between chromophobe RCC and oncocytoma, the method comprising: obtaining a biological sample from a subject; determining in said sample an expression profile of nucleic acid sequences selected from the group consisting of SEQ ID NOS: 14-15, 28-35, a fragment thereof or a sequence having at least 80% identity thereto; and comparing said expression profile to a reference value; whereby a relative abundance of said nucleic acid sequences allows the detection of said oncocytoma or chromophobe RCC.

According to some embodiments, a relative abundance of nucleic acid sequences selected from the group consisting of SEQ ID NOS: 14-15, 28-31 is indicative of the presence of oncocytoma.

According to other embodiments, a relative abundance of nucleic acid sequences selected from the group consisting of SEQ ID NOS: 32-35 is indicative of the presence of chromophobe RCC.

The invention further provides a method for distinguishing between clear cell RCC and oncocytoma, the method comprising: obtaining a biological sample from a subject; determining in said sample an expression profile of nucleic acid sequences selected from the group consisting of SEQ ID NOS: 1-3, 6, 7, 11, 13, 16, 17, 19-27, 30, 31, 36-40, 47-49, a fragment thereof or a sequence having at least 80% identity thereto; and comparing said expression profile to a reference value; whereby a relative abundance of said nucleic acid sequences allows the detection of said oncocytoma or clear cell RCC.

According to some embodiments, a relative abundance of nucleic acid sequences selected from the group consisting of SEQ ID NO: 13, 19, 25-27, 30, 31, 36-40, 48 is indicative of the presence of oncocytoma.

According to other embodiments, a relative abundance of nucleic acid sequences selected from the group consisting of SEQ ID NOS: 1-3, 6, 7, 11, 16, 17, 20-24, 47, 49 is indicative of the presence of clear cell RCC.

The invention further provides a method for distinguishing between chromophobe RCC and clear cell RCC, the method comprising: obtaining a biological sample from a subject; determining in said sample an expression profile of nucleic acid sequences selected from the group consisting of SEQ ID NOS: 1-3, 6, 7, 22, 23, 32-37, 43, 44, a fragment thereof or a sequence having at least 80% identity thereto; and comparing said expression profile to a reference value; whereby a relative abundance of said nucleic acid sequences allows the detection of said RCC.

According to some embodiments, a relative abundance of nucleic acid sequences selected from the group consisting of SEQ ID NOS: 1-3, 6, 7, 22, 23 is indicative of the presence of clear cell RCC.

According to other embodiments, a relative abundance of nucleic acid sequences selected from the group consisting of SEQ ID NOS: 32-37, 43, 44 is indicative of the presence of chromophobe RCC.

The invention further provides a method for distinguishing between clear cell RCC and papillary RCC, the method comprising: obtaining a biological sample from a subject; determining in said sample an expression profile of nucleic acid sequences selected from the group consisting of SEQ ID NOS: 4, 5, 8, 9, 30, 31, 41, 42, 50, 51, a fragment thereof or a sequence having at least 80% identity thereto; and comparing said expression profile to a reference value; whereby a relative abundance of said nucleic acid sequences allows the detection of said RCC.

According to some embodiments, a relative abundance of nucleic acid sequences selected from the group consisting of SEQ ID NOS: 41, 42 is indicative of the presence of clear cell RCC.

According to other embodiments, a relative abundance of nucleic acid sequences selected from the group consisting of SEQ ID NOS: 4, 5, 8, 9, 30, 31, 50, 51, is indicative of the presence of papillary RCC.

The invention further provides a method for distinguishing between chromophobe RCC and papillary RCC, the method comprising: obtaining a biological sample from a subject; determining in said sample an expression profile of nucleic acid sequences selected from the group consisting of SEQ ID NOS: 1-5, 8-11, 13, 24-27, 30-35, 43, 44, 47, 49, 52, 53, a fragment thereof or a sequence having at least 80% identity thereto; and comparing said expression profile to a reference value; whereby a relative abundance of said nucleic acid sequences allows the detection of said RCC.

According to some embodiments, a relative abundance of nucleic acid sequences selected from the group consisting of SEQ ID NOS: 13, 25-27, 32-35, 43, 44, 52, 53, is indicative of the presence of chromophobe RCC.

According to some embodiments, a relative abundance of nucleic acid sequences selected from the group consisting of SEQ ID NOS: 1-5, 8-11, 24, 30, 31, 47, 49 is indicative of the presence of papillary RCC.

The invention further provides a method for distinguishing between papillary RCC and oncocytoma, the method comprising: obtaining a biological sample from a subject; determining in said sample an expression profile of nucleic acid sequences selected from the group consisting of SEQ ID NOS: 4, 5, 8-13, 25-27, 41-42, 45-47, a fragment thereof or a sequence having at least 80% identity thereto; and comparing said expression profile to a reference value; whereby a relative abundance of said nucleic acid sequences allows the detection of said papillary RCC or oncocytoma.

According to some embodiments, a relative abundance of nucleic acid sequences selected from the group consisting of SEQ ID NOS: 4, 5, 8-11, 45-47, is indicative of the presence of papillary RCC.

According to other embodiments, a relative abundance of nucleic acid sequences selected from the group consisting of SEQ ID NOS: 12, 13, 25-27, 41-42, is indicative of the presence of oncocytoma.

The invention further provides a method for distinguishing between chromophobe RCC, clear cell RCC, papillary RCC and oncocytoma, the method comprising: obtaining a biological sample from a subject; determining in said sample an expression profile of nucleic acid sequences selected from the group consisting of SEQ ID NOS: 4, 5, 13-15, 20, 21, 25, 34, 35, 41, 42; a fragment thereof and a sequence having at least 80% identity thereto; and comparing said expression profile to a reference value; whereby a relative abundance of said nucleic acid sequences allows the detection of said RCC.

In certain embodiments, the subject is a human.

In certain embodiments, the method is used to determine a course of treatment of the subject.

According to other embodiments, said biological sample is selected from the group consisting of bodily fluid, a cell line and a tissue sample. According to some embodiments, said tissue is a fresh, frozen, fixed, wax-embedded or formalin fixed paraffin-embedded (FFPE) tissue.

According to some embodiments said tissue sample is a kidney tumor sample.

According to some embodiments said tissue sample is selected from the group consisting of benign renal tissue sample and malignant renal tissue sample.

According to some embodiments, the method comprises determining the expression levels of at least one nucleic acid sequence. According to some embodiments the method further comprising combining one or more expression ratios. According to some embodiments, the expression levels are determined by a method selected from the group consisting of nucleic acid hybridization, nucleic acid amplification, and a combination thereof. According to some embodiments, the nucleic acid hybridization is performed using a solid-phase nucleic acid biochip array. According to certain embodiments, the nucleic acid hybridization is performed using in situ hybridization. According to some embodiments, the in situ hybridization method comprises hybridization with a probe. According to other embodiments, the probe comprises a nucleic acid sequence that is complementary to a sequence selected from the group consisting of SEQ ID NOS: 1-75 and sequences at least about 80% identical thereto.

According to other embodiments, the nucleic acid amplification method is real-time PCR (RT-PCR). According to one embodiment, said real-time PCR is quantitative real-time PCR (qRT-PCR).

According to some embodiments, the RT-PCR method comprises forward and reverse primers. According to other embodiments, the forward primer comprises a sequence selected from the group consisting of SEQ ID NOS: 82-87, a fragment thereof and a sequence having at least about 80% identity thereto. According to other embodiments, the reverse primer comprises SEQ ID NO: 90, a fragment thereof and a sequence having at least about 80% identity thereto.

According to some embodiments, the real-time PCR method further comprises hybridization with a probe. According to other embodiments, the probe comprises a nucleic acid sequence that is complementary to a sequence selected from the group consisting of SEQ ID NOS: 1-75, a fragment thereof and sequences at least about 80% identical thereto.

According to other embodiments, the probe comprises a sequence selected from the group consisting of any one of SEQ ID NOS: 76-81, a fragment thereof and sequences at least about 80% identical thereto.

The invention further provides a kit for renal tumor classification, said kit comprises a probe comprising a nucleic acid sequence that is complementary to a sequence selected from the group consisting of SEQ ID NOS: 1-75, a fragment thereof and sequences having at least about 80% identity thereto.

According to some embodiments, said probe comprising a nucleic acid sequence selected from the group consisting of SEQ ID NOS: 76-81, a fragment thereof and a sequence at least about 80% identical thereto.

According to some embodiments, the kit further comprises forward and reverse primers. According to some embodiments, the forward primer comprising a sequence selected from the group consisting of SEQ ID NOS: 82-87, a fragment thereof and a sequence having at least about 80% identity thereto.

According to other embodiments, the reverse primer comprises SEQ ID NO: 90, a fragment thereof and sequences having at least about 80% identity thereto.

These and other embodiments of the present invention will become apparent in conjunction with the figures, description and claims that follow.

The results are based on microarray analysis. Statistically significant miRs with p-value smaller than 0.0417 and at least 4-fold change in expression are marked with circles: hsa-miR-139-5p (SEQ ID NO: 14), hsa-miR-551b (SEQ ID NO: 30), hsa-miR-141 (SEQ ID NO: 32), hsa-miR-200b (SEQ ID NO: 54), hsa-miR-637 (SEQ ID NO: 56), hsa-miR-373* (SEQ ID NO: 58) and hsa-miR-200c (SEQ ID NO: 34).

FIGS. 3A-3D demonstrate separation between histological types using a small set of microRNAs. The training set included oncocytoma samples ("O", n=21, stars), chromophobe tumors ("H", n=13, diamonds), conventional cell tumors ("C", n=17, squares), and papillary tumors ("P", n=20, circles). Plotting the expression of hsa-miR-221 (SEQ ID NO: 25), hsa-miR-31 (SEQ ID NO: 4) and hsa-miR-200c (SEQ ID NO: 34) in each of the training set samples (FIG. 3A), the four types of samples group into areas with distinct ranges of expression. Box-plots (FIGS. 3B, 3C and 3D) indicate expression levels of microRNAs in the four histological types (same samples as in FIG. 3A), showing the median value (horizontal line), 25 to 75 percentile (box), extent of data ("whiskers") and outliers (crosses). hsa-miR-221 (SEQ ID NO: 25) and hsa-miR-210 (SEQ ID NO: 20) (FIG. 3B) have distinct expression in oncocytomas and chromophobe tumors compared to conventional cell and papillary tumor, with hsa-miR-221 more strongly expressed in oncocytomas and chromophobe tumors, and hsa-miR-210 more strongly expressed in conventional cell and papillary tumors. hsa-miR-139-5p (SEQ ID NO: 14) and hsa-miR-200c (SEQ ID NO: 34) (FIG. 3C) have distinct expression in oncocytomas compared to chromophobe tumors, with hsa-miR-139-5p more strongly expressed in oncocytomas and hsa-miR-200c more strongly expressed in chromophobe tumors. hsa-miR-126 (SEQ ID NO: 41) and hsa-miR-31 (SEQ ID NO: 4) (FIG. 3D) have distinct expression in conventional cell tumors compared to papillary tumors, with hsa-miR-126 more strongly expressed in conventional cell tumors and hsa-miR-31 more strongly expressed in papillary tumors.

FIGS. 4A-4D show classification of kidney tumors using expression levels of six microRNAs as detected by microarray.

Figure 4A:
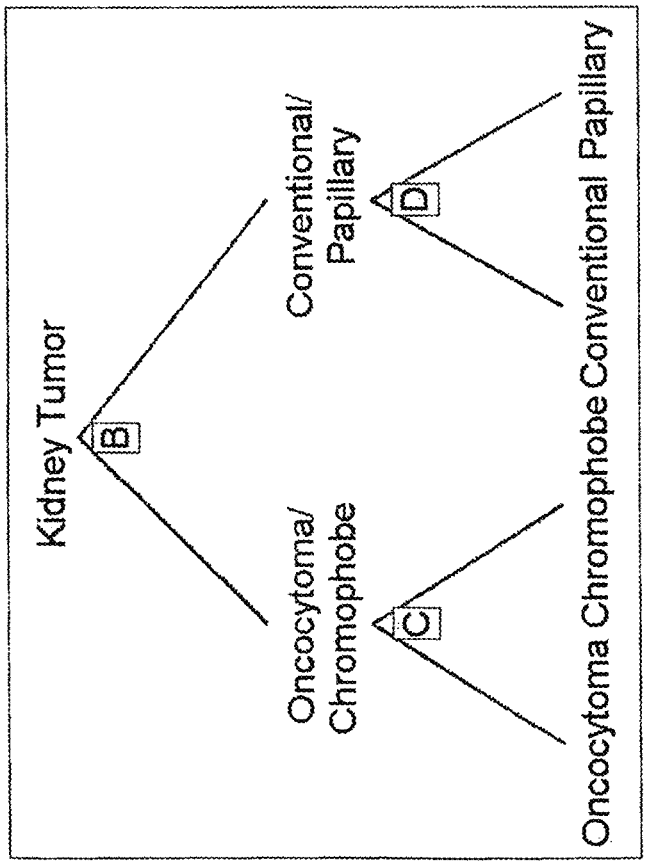
Figure 4B:
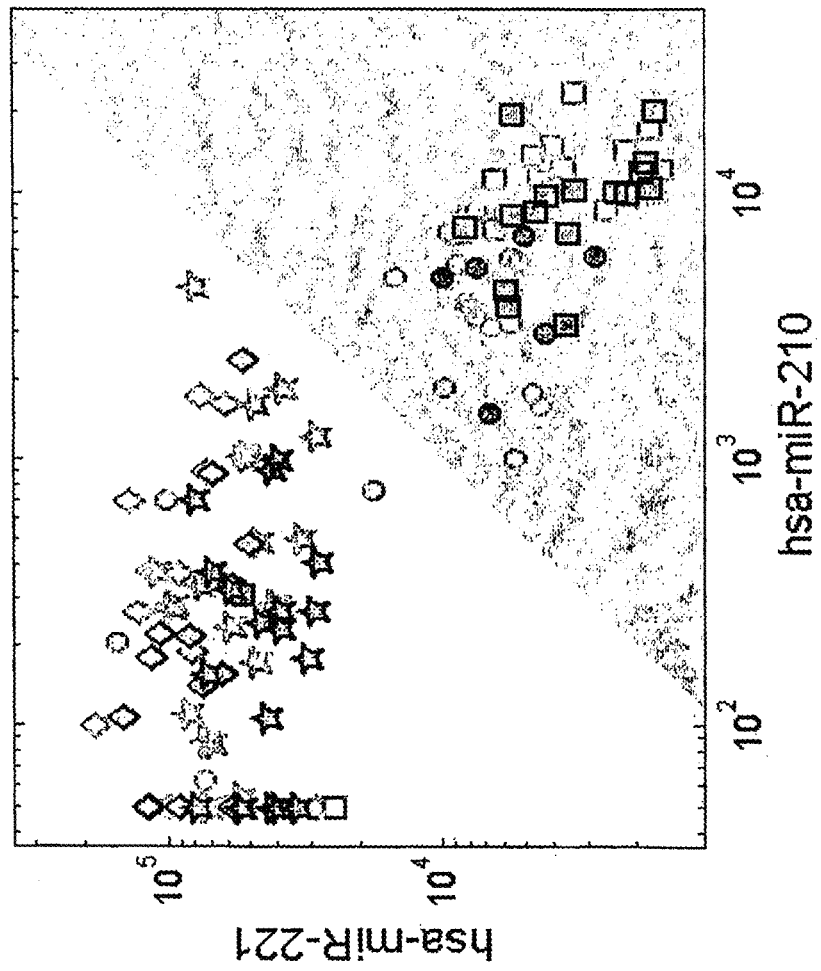
Figure 4C:
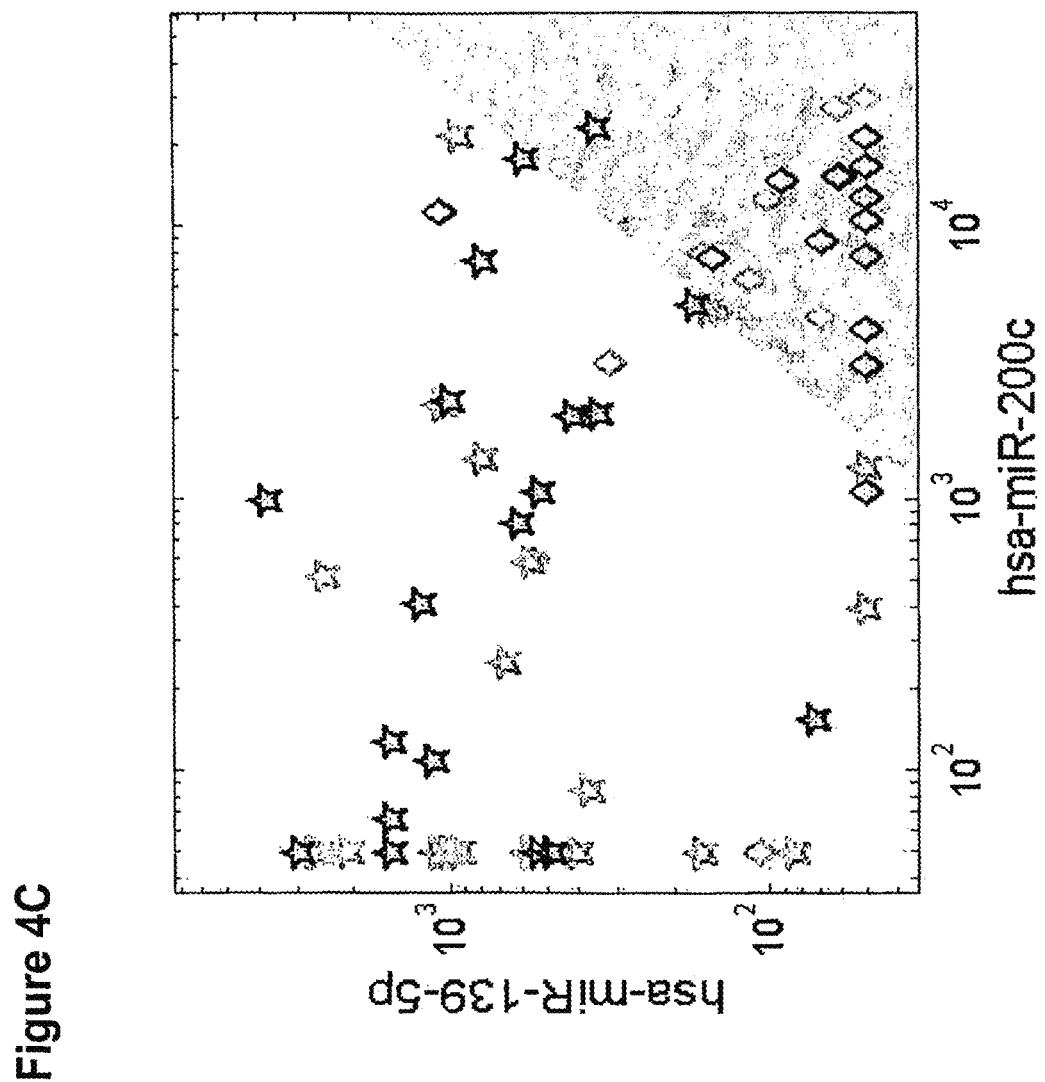
Figure 4D:
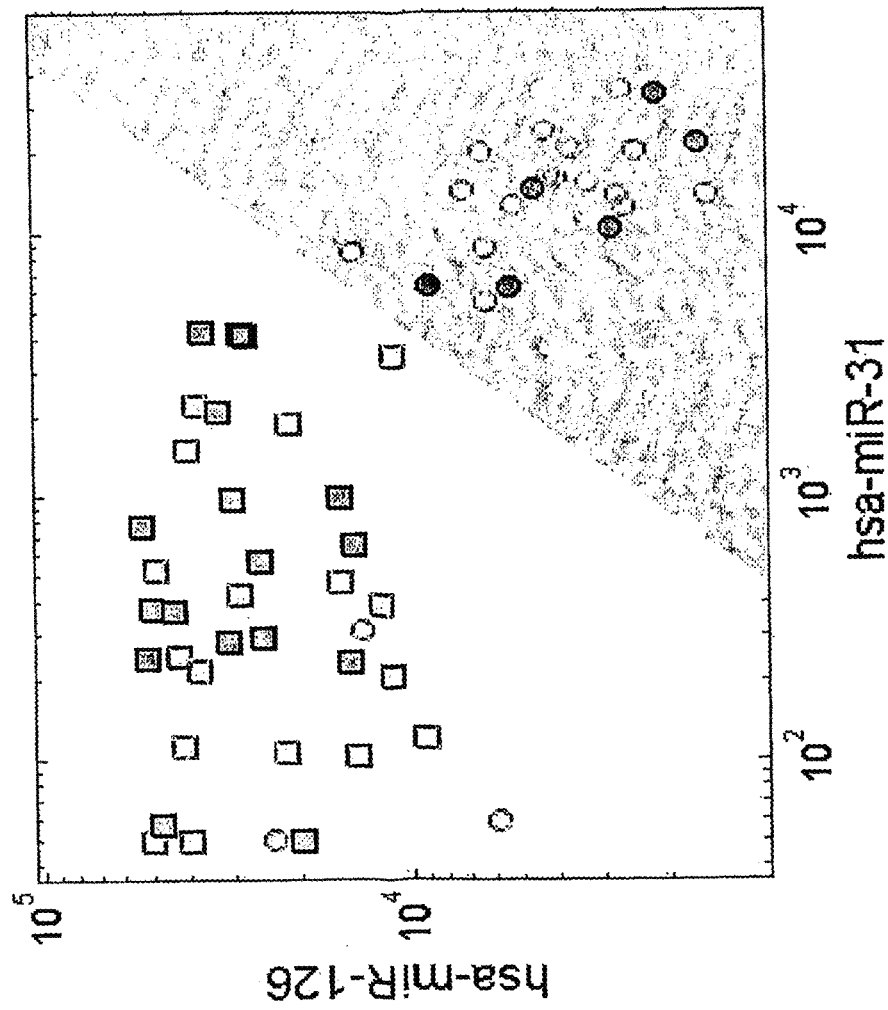

FIG. 4A) Classification proceeds in two steps, following the cluster structure of the histological types: first, samples are classified into either the oncocytoma/chromophobe pair, or the conventional/papillary pair, using expression levels of hsa-miR-210 (SEQ ID NO: 20) and hsa-miR-221 (SEQ ID NO: 25) (FIG. 4B). In the second step, oncocytoma is identified from chromophobe using expression levels of hsa-miR-200c (SEQ ID NO: 34) and hsa-miR-139-5p (SEQ ID NO: 14) (FIG. 4C), and conventional cell is identified from papillary using expression levels of hsa-miR-31 (SEQ ID NO: 4) and hsa-miR-126 (SEQ ID NO: 41) (FIG. 4D). Independent test samples included oncocytoma samples (n=19, stars), chromophobe tumors (n=14, diamonds), conventional cell tumors (n=17, squares), and papillary tumors (n=6, circles). The grey regions indicate the thresholds for classification for each pair of microRNAs, indicating in each case the right branch in the binary classification that $M_i^k=F^k(S_i^k)$. Statistical analysis is performed in log-space. For presentation and calculation of fold-change, data is translated back to linear-space by taking the exponent.

Figure 5A:
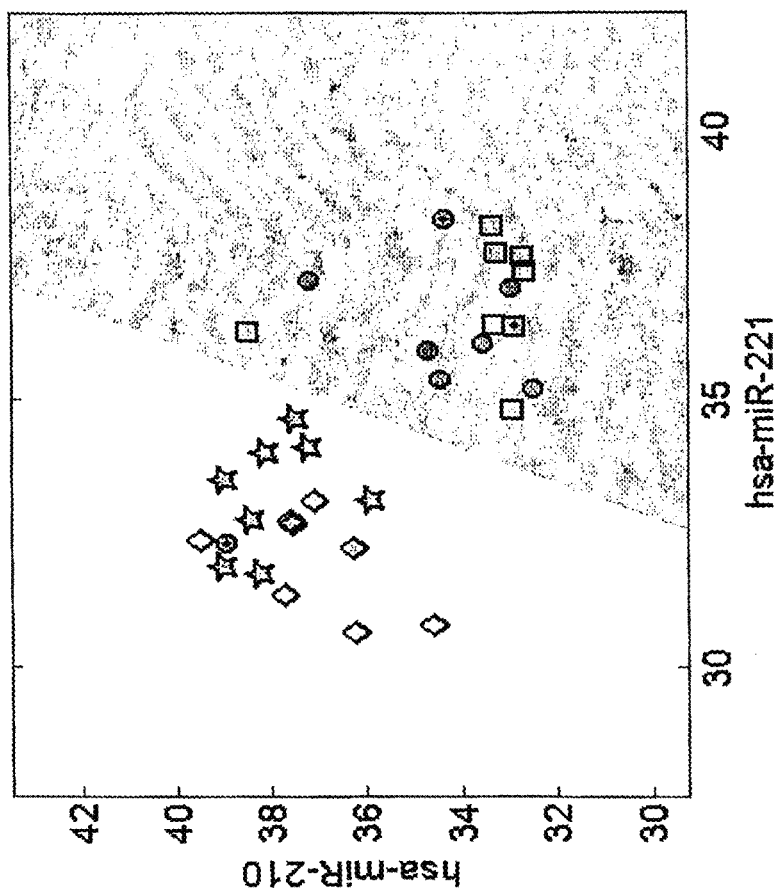
Figure 5B:
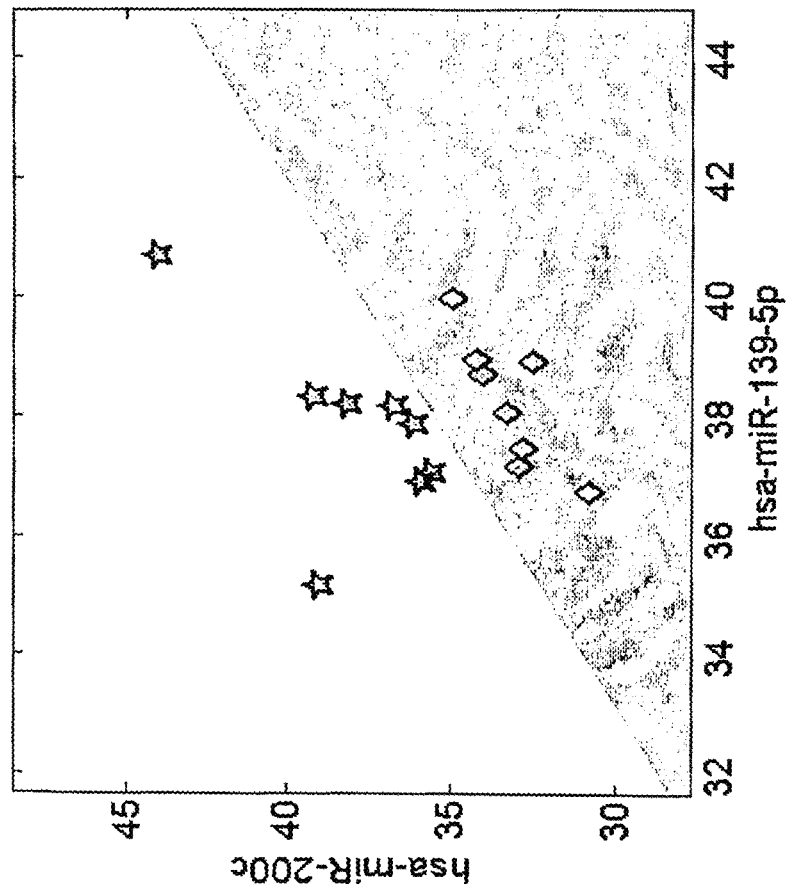
Figure 5C:
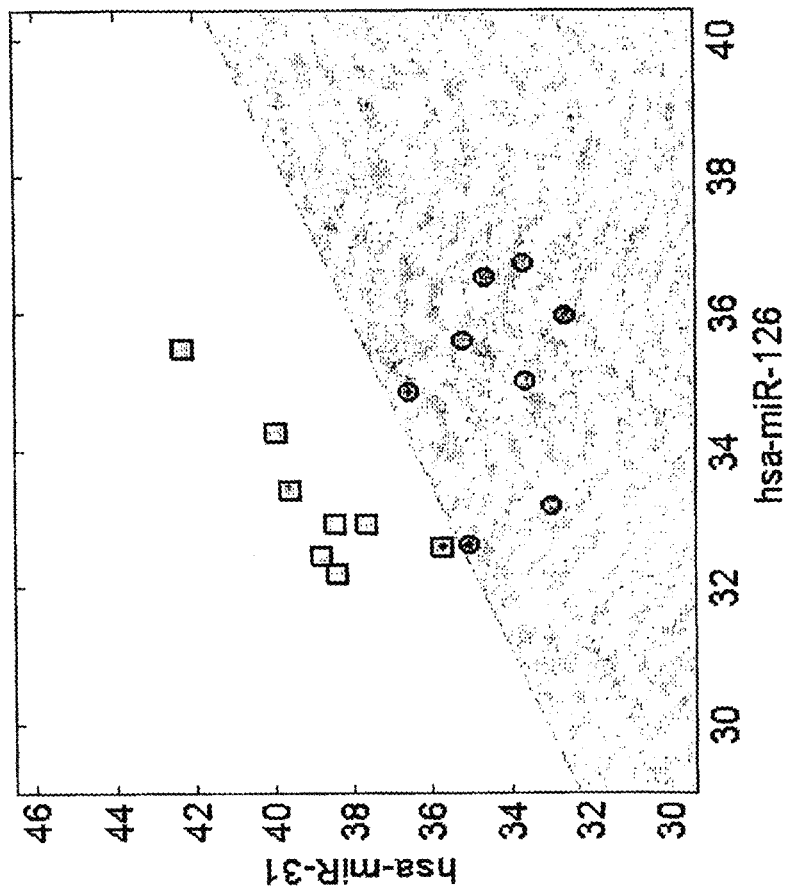

FIGS. 5A-5C show classification of kidney tumors using expression levels of six microRNAs as detected by qRT-PCR. FIG. 5A demonstrates Node 1 in the classification tree (as presented in FIG. 4A)—classification of oncocytoma (stars) and chromophobe (diamonds) samples from conventional cell (squares) and papillary (circles) samples using expression levels of hsa-miR-210 (SEQ ID NO: 20) and hsa-miR-221 (SEQ ID NO: 25). A logistic regression classifier was used in order to obtain a threshold. The black dots denote samples that got an erroneous classification using LOOCV (in the entire tree; not specifically in the current node).

FIG. 5B demonstrates Node 2 in the classification tree—classification of oncocytoma (stars) from chromophobe (diamonds) samples using hsa-miR-200c (SEQ ID NO: 34) and hsa-miR-139-5p (SEQ ID NO: 14). A logistic regression classifier was used in order to obtain a threshold.

FIG. 5C demonstrates Node 3 in the classification tree—classification of conventional cell (squares) from papillary (circles) samples using hsa-miR-31 (SEQ ID NO: 4) and hsa-miR-126 (SEQ ID NO: 41). A logistic regression classifier was used in order to obtain a threshold. The black dots denote samples that got an erroneous classification using LOOCV (in the entire tree; not specifically in the current node).

DETAILED DESCRIPTION OF THE INVENTION

The invention is based on the discovery that specific nucleic acid sequences (SEQ ID NOS: 1-90) can be used for the classification of kidney tumors. The present invention provides a sensitive, specific and accurate method which can be used to distinguish between particular subtypes of kidney tumors.

Renal cell cancer comprise of different subtypes of cancers that differ in genetic background, response to surgical and medical therapy and prognosis. The different histological subclasses of RCC are associated with the different disease specific survival that range from 24% to 100% at 5 years from surgery. While non conventional types RCC have a lower pathological stage and reduced portion of metastatic disease, its response to systemic medical therapy is reduced compared to conventional type RCC. Various markers have been suggested and used for this distinction between histology subtypes, but these show mixed or limited specificities, and a significant fraction of samples may be unclassified or misclassified. Unclassified RCC comprise of up to 6% of all RCC even in series from centers of excellence and have the worst clinical outcome as compared to other subclasses. One can assume that the proportion of unclassified RCC is higher in centers lacking dedicated pathologists focusing in genitourinary malignancies and therefore emphasizes that need for additional diagnostic tools for RCC subclassification.

According to the present invention, a new microRNA-based classifier was developed for determining the specific subtypes of kidney tumors. The classifier uses a transparent algorithm and allows a clear interpretation of the specific biomarkers.

The microRNA-based classifier reached an accuracy of 93% in histological classification of an independent set of 56 test samples. This diagnostic model can potentially be used at preoperative and postoperative setting in order to differentiate the 4 major RCC subtypes, and may be a useful clinical tool for the diagnosis and management of renal tumor cases.

The differentially expressed microRNAs can provide clues to the biological differences between the subtypes, their diverging oncogenetic processes and possible new targets for type specific target therapy. It was found that hsa-miR-141 (SEQ ID NO: 32) and hsa-miR-200c (SEQ ID NO: 34) are specifically expressed in the chromophobe tumors. hsa-miR-221 (SEQ ID NO: 25) and hsa-miR-222 (SEQ ID NO: 26) are strongly expressed in both chromophobe and oncocytoma types. These microRNAs inhibit erythropoietic growth by targeting and down-regulating the KIT receptor. Interestingly, KIT was found to be expressed specifically in oncocytoma and chromophobe subtypes of RCC. Other microRNAs show strong differences in expression between the subtypes (Table 2), but their involvement in the oncogenic process is not clear. Some clues or links to other known pathways may be found through transcription factors that potentially regulate these microRNAs (Table 3).

The possibility to distinguish between different subtypes of kidney tumors facilitates providing the patient with the best and most suitable treatment.

The present invention provides diagnostic assays and methods, both quantitative and qualitative for detecting, diagnosing, monitoring, staging and prognosticating kidney cancers by comparing levels of the specific microRNA molecules of the invention. Such levels are preferably measured in at least one of biopsies, tumor samples, cells, tissues and/or bodily fluids. The present invention provides methods for diagnosing the presence of a specific kidney cancer by analyzing the levels of said microRNA molecules in biopsies, tumor samples, cells, tissues or bodily fluids.

In the present invention, determining the levels of said microRNAs in biopsies, tumor samples, cells, tissues or bodily fluid, is particularly useful for discriminating between different subtypes of kidney tumors.

All the methods of the present invention may optionally further include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, but are not limited to, radioimmunoassays, reverse transcriptase PCR (RT-PCR) assays, immunohistochemistry assays, in situ hybridization assays, competitive-binding assays, Northern Blot analyses, ELISA assays, nucleic acid microarrays and biochip analysis.

An arbitrary threshold on the expression level of one or more nucleic acid sequences can be set for assigning a sample or tumor sample to one of two groups. Alternatively, in a preferred embodiment, expression levels of one or more nucleic acid sequences of the invention are combined by taking ratios of expression levels of two nucleic acid sequences and/or by a method such as logistic regression to define a metric which is then compared to previously measured samples or to a threshold. The threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled and provides diagnostic information on the likelihood that a samples belongs to a certain class of renal subtype. In multivariate analysis, the microRNA signature provides a high level of prognostic information.

DEFINITIONS

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +1-10%.

Attached

"Attached" or "immobilized" as used herein to refer to a probe and a solid support means that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, blood fraction, plasma, serum, sputum, stool, tears, mucus, hair, skin, urine, effusions, ascitic fluid, amniotic fluid, saliva, cerebrospinal fluid, cervical secretions, vaginal secretions, endometrial secretions, gastrointestinal secretions, bronchial secretions, cell line, tissue sample, or secretions from the breast. A biological sample may be provided by removing a sample of cells from a subject but can also be accomplished by using previously isolated cells (e.g., isolated by another person, at another time, and/or for another purpose), or by performing the methods described herein in vivo. Archival tissues, such as those having treatment or outcome history, may also be used. Biological samples also include explants and primary and/or transformed cell cultures derived from animal or human tissues.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are not limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, clear cell RCC, papillary RCC and chromophobe RCC, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc) and based on a statistical model and/or a training set of previously labeled items.

Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary means 100% complementary base pairing between nucleotides or nucleotide analogs of nucleic acid molecules.

$C_T$ $C_T$ signals represent the first cycle of PCR where amplification crosses a threshold (cycle threshold) of fluorescence. Accordingly, low values of $C_T$ represent high abundance or expression levels of the microRNA.

In some embodiments the PCR $C_T$ signal is normalized such that the normalized $C_T$ remains inversed from the expression level. In other embodiments the PCR $C_T$ signal may be normalized and then inverted such that low normalized-inverted $C_T$ represents low abundance or expression levels of the microRNA.

Data Processing Routine

As used herein, a "data processing routine" refers to a process that can be embodied in software that determines the biological significance of acquired data (i.e., the ultimate results of an assay or analysis). For example, the data processing routine can make determination of tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis. These numerical values associated with analysis may be values such as peak height and area under the curve.

Data Structure

As used herein the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means determining the level of a component, either quantitatively or qualitatively.

Differential Expression

"Differential expression" means qualitative or quantitative differences in the temporal and/or spatial gene expression patterns within and among cells and tissue. Thus, a differentially expressed gene may qualitatively have its expression altered, including an activation or inactivation, in, e.g., normal versus diseased tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs needs only be large enough to quantify via standard characterization techniques such as expression arrays, quantitative reverse transcriptase PCR, Northern blot analysis, real-time PCR, in situ hybridization and RNase protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cDNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. According to some embodiments, the term "expression profile" means measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid or polypeptide. Thus, a fragment is itself also a nucleic acid or polypeptide, respectively.

Gene

"Gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Identity

"Identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA sequences, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

Label

"Label" as used herein means a composition detectable by spectroscopic, photochemical, biochemical, immunochemical, chemical, or other physical means. For example, useful labels include $P^{32}$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e. the ratio of the probability of belonging to the first group (P) over the probability of belonging to the second group (1−P), as a linear combination of the different expression levels (in log-space). The logistic regression output can be used as a classifier by prescribing that a case or sample will be classified into the first type is P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Nucleic Acid

"Nucleic acid" or "oligonucleotide" or "polynucleotide", as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated herein by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-OH-group may be replaced by a group selected from H, OR, R, halo, SH, SR, NH2, NHR, NR2 or CN, wherein R is C1-C6 alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe" as used herein means an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Value

As used herein the term "reference value" means a value that statistically correlates to a particular outcome when compared to an assay result. In preferred embodiments the reference value is determined from statistical analysis of studies that compare microRNA expression with known clinical outcomes.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"Specificity" used herein may mean a statistical measure of how well a binary classification test correctly identifies a condition, for example how frequently it correctly classifies a cancer into the correct type out of two possible types. The specificity for class A is the proportion of cases that are determined to belong to class "not A" by the test out of the cases that are in class "not A", as determined by some absolute or gold standard.

Stage of Cancer

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

Stringent Hybridization Conditions

"Stringent hybridization conditions" as used herein mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" as used herein means that a first and a second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subtype of Cancer

As used herein, the term "subtype of cancer" refers to different types of cancer that effect the same organ (e.g., spindle cell, cystic and collecting duct carcinomas of the kidney).

Subject

As used herein, the term "subject" refers to a mammal, including both human and other mammals. The methods of the present invention are preferably applied to human subjects.

Target Nucleic Acid

"Target nucleic acid" as used herein means a nucleic acid or variant thereof that may be bound by another nucleic acid. A target nucleic acid may be a DNA sequence. The target nucleic acid may be RNA. The target nucleic acid may comprise a mRNA, tRNA, shRNA, siRNA or Piwi-interacting RNA, or a pri-miRNA, pre-miRNA, miRNA, or anti-miRNA.

The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Threshold Expression Profile

As used herein, the phrase "threshold expression profile" refers to a criterion expression profile to which measured values are compared in order to classify a tumor.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Tumor

"Tumor" as used herein, refers to all neoplastic cell growth and proliferation, whether malignant or benign, and all precancerous and cancerous cells and tissues.

Variant

"Variant" as used herein referring to a nucleic acid means (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild type" sequence refers to a coding, a non-coding or an interface sequence which is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNAs for the identification, classification and diagnosis of specific cancers and the identification of their tissues of origin.

microRNA Processing

A gene coding for microRNA (miRNA) may be transcribed leading to production of a miRNA primary transcript known as the pri-miRNA. The pri-miRNA may comprise a hairpin with a stem and loop structure. The stem of the hairpin may comprise mismatched bases. The pri-miRNA may comprise several hairpins in a polycistronic structure.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA: miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acids

Nucleic acids are provided herein. The nucleic acids comprise the sequences of SEQ ID NOS: 1-90 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from about 10 to about 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

TABLE 1

The nucleic acids of the invention (miRs and hairpins)

| miR Name | miR SEQ ID NO: | Hairpin SEQ ID NO: |
|---|---|---|
| hsa-miR-194 | 1 | 2, 3 |
| hsa-miR-31 | 4 | 5 |
| hsa-miR-192 | 6 | 7 |
| hsa-miR-204 | 8 | 9 |
| hsa-mir-21* | 10 | 11 |
| hsa-miR-221* | 12 | 13 |
| hsa-miR-139-5p | 14 | 15 |
| hsa-miR-146b-5p | 16 | 17 |
| hsa-miR-10a* | 18 | 19 |
| hsa-miR-210 | 20 | 21 |
| hsa-miR-155 | 22 | 23 |
| hsa-miR-455-3p | 24 | 49 |

TABLE 1-continued

The nucleic acids of the invention (miRs and hairpins)

| miR Name | miR SEQ ID NO: | Hairpin SEQ ID NO: |
|---|---|---|
| hsa-miR-221 | 25 | 13 |
| hsa-miR-222 | 26 | 27 |
| hsa-miR-140-5p | 28 | 29 |
| hsa-miR-551b | 30 | 31 |
| hsa-miR-141 | 32 | 33 |
| hsa-miR-200c | 34 | 35 |
| hsa-miR-182 | 36 | 37 |
| MID-00536 | 38 | 39, 40 |
| hsa-miR-126 | 41 | 42 |
| hsa-miR-187 | 43 | 44 |
| hsa-miR-146a | 45 | 46 |
| hsa-miR-21 | 47 | 11 |
| hsa-miR-10a | 48 | 19 |
| hsa-miR-138 | 50 | 51 |
| hsa-miR-150* | 52 | 53 |
| hsa-miR-200b | 54 | 55 |
| hsa-miR-637 | 56 | 57 |
| hsa-miR-373* | 58 | 59 |
| hsa-miR-371-5p | 60 | 61 |
| hsa-miR-557 | 62 | 63 |
| hsa-miR-193b | 64 | 65 |
| hsa-miR-365 | 66 | 67 |
| hsa-miR-30b | 68 | 69 |
| hsa-miR-196b | 70 | 71 |
| hsa-miR-200a | 72 | 73 |
| hsa-miR-483-5p | 74 | 75 | miR name: is the miRBase registry name (release 10)
MID-00536 is not presented in the miRBase registry. It was cloned in Rosetta Genomics.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise any of the sequences of SEQ ID NOS: 1-75 or variants thereof.

The pri-miRNA may comprise a hairpin structure. The hairpin may comprise a first and a second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy of less than −25 Kcal/mole as calculated by the Vienna algorithm with default parameters, as described in Hofacker et al., Monatshefte f Chemie 125: 167-188 (1994), the contents of which are incorporated herein by reference. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-75 or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1, 4, 6, 8, 10, 12, 14, 16, 18, 20, 22, 24, 25, 26, 28, 30, 32, 34, 36, 38, 41, 43, 45, 47, 48, 50, 52, 54, 56, 58, 60, 62, 64, 66, 68, 70, 72, and 74, or variants thereof.

Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 76-81; or variants thereof.

Linker Sequences

The probe may further comprise a linker. The linker may be 10-60 nucleotides in length.

The linker may be 20-27 nucleotides in length. The linker may be of sufficient length to allow the probe to be a total length of 45-60 nucleotides. The linker may not be capable of forming a stable secondary structure, or may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription Using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription Using Polyadenylated Sequence Ligated to RNA

Polyadenylated RNA may be used in a reverse transcription (RT) reaction using a poly(T) primer comprising a 5' adaptor sequence. The poly(T) sequence may comprise 8, 9, 10, 11, 12, 13, or 14 consecutive thymines.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid.

The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides. The forward primer may comprise SEQ ID NOS: 82-89; or variants thereof.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise SEQ ID NO: 90 or variants thereof.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostics

As used herein the term "diagnosing" refers to classifying pathology, or a symptom, determining a severity of the pathology (grade or stage), monitoring pathology progression, forecasting an outcome of pathology and/or prospects of recovery.

As used herein the phrase "subject in need thereof" refers to an animal or human subject who is known to have cancer, at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

Analyzing presence of malignant or pre-malignant cells can be effected in-vivo or ex-vivo, whereby a biological sample (e.g., biopsy) is retrieved. Such biopsy samples comprise cells and may be an incisional or excisional biopsy. Alternatively the cells may be retrieved from a complete resection.

While employing the present teachings, additional information may be gleaned pertaining to the determination of treatment regimen, treatment course and/or to the measurement of the severity of the disease.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

A method of diagnosis is also provided. The method comprises detecting an expression level of a specific cancer-associated nucleic acid in a biological sample. The sample may be derived from a patient. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue sections may be performed. When comparing the fingerprints between individual samples the skilled artisan can make a diagnosis, a prognosis, or a prediction based on the findings. It is further understood that the nucleic acid sequence which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly (T) primer, a forward primer, a reverse primer, and a probe.

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, components for in situ hybridization and components for isolating miRNA. Other kits of the invention may include components for making a nucleic acid array comprising miRNA, and thus, may include, for example, a solid support.

The following examples are presented in order to more fully illustrate some embodiments of the invention. They should, in no way be construed, however, as limiting the broad scope of the invention.

EXAMPLES

Materials and Methods

1. Tumor Samples 127 renal tumor FFPE samples were obtained from the pathology archives of Sheba Medical Center (Tel-Hashomer, Israel) and commercial sources (ABS Inc., Wilmington, Del., and BioServe™, Beltsville, Md.). The study protocol was approved by the Research Ethics Board of each of the contributing institutes. FFPE samples were reviewed by a pathologist with experience in urological pathology for histological type based on hematoxilin-eosin (H&E) stained slides, performed on the first and/or last sections of the sample. Tumor classification was based on the World Health Organization (WHO) guidelines (12). Tumor content was higher than 60% for all the samples and higher than 80% for >80% of the samples.

The differential microRNAs were identified and the classification algorithm was trained using 71 samples including 21 oncocytoma samples, 13 chromophobe samples, 17 conventional cell samples, and 20 papillary samples. The classification algorithm was tested on an independent set of 56 samples including 19 oncocytoma samples, 14 chromophobe samples, 17 conventional cell samples and 6 papillary samples 2. RNA Extraction Total RNA was isolated as previously described (Rosenfeld et al., 2008). Briefly, seven to ten 10 μm-thick tissue sections were incubated a few times in xylene at 57° C. to remove excess paraffin, then washed several times with ethanol. Proteins were degraded by incubating the sample in a proteinase K solution at 45° C. for a few hours. RNA was extracted using acid phenol/chloroform and then precipitated using ethanol; DNAses were introduced to digest DNA. Total RNA quantity and quality was measured by Nanodrop ND-1000 (NanoDrop Technologies, Wilmington, Del.).

3. MicroRNA Profiling

Custom microarrays were produced by printing DNA oligonucleotide probes to more than 600 human microRNAs. Each probe, printed in triplicate, carries up to 22-nucleotide (nt) linker at the 3' end of the microRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides using a Genomic Solutions® BioRobotics MicroGrid II according the MicroGrid manufacturer's directions. 54 negative control probes were designed using the sense sequences of different microRNAs. Two groups of positive control probes were designed to hybridize to microarray (i) synthetic small RNA were spiked to the RNA before labeling to verify the labeling efficiency and (ii) probes for abundant small RNA (e.g. small nuclear RNAs (U43, U49, U24, Z30, U6, U48, U44), 5.8 s and 5 s ribosomal RNA) were spotted on the array to verify RNA quality. The slides were blocked in a solution containing 50 mM ethanolamine, 1M Tris (pH9.0) and 0.1% SDS for 20 min at 50° C., then thoroughly rinsed with water and spun dry.

4. Cy-Dye Labeling of miRNA for Microarray

Five μg of total RNA were labeled by ligation (Thomson et al., Nature Methods 2004, 1:47-53) of an RNA-linker, p-rCrU-Cy/dye (Dharmacon), to the 3'-end with Cy3 or Cy5. The labeling reaction contained total RNA, spikes (0.1-20 fmoles), 300 ng RNA-linker-dye, 15% DMSO, 1x ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 min and than added on top of the miRdicator™ array. Slides were hybridized 12-16 hr in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm at 100% power). Array images were analyzed using SpotReader software (Niles Scientific).

5. Array Data Normalization

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the mean expression level for each probe in two representative samples, one from each tumor type.

For each sample k with data vector $S^k$, a 2nd degree polynomial $F^k$ was found so as to provide the best fit between the sample data and the reference data, such that $R \approx F^k(S^k)$. Remote data points ("outliers") were not used for fitting the polynomials F. For each probe in the sample (element $S_i^k$ in the vector $S^k$), the normalized value (in log-space) Mk is calculated from the initial value $S_i^k$ by transforming it with the polynomial function $F^k$, so that $M_i^k = F^k(S_i^k)$. Statistical analysis is performed in log-space. For presentation and calculation of fold-change, data is translated back to linear-space by taking the exponent.

6. Statistical Analysis

For every pair of groups (e.g., oncocytoma vs. chromophobe or conventional cell vs. papillary), microRNA expression was compared for all microRNAs that had expression level above background (median normalized fluorescence signal>700) in at least one of the two groups. P-values were calculated using a two-sided (unpaired) Student's t-test on the log-transformed normalized fluorescence signal. The threshold for significant differences was determined by setting a False Discovery Rate (FDR) of 0.1, to correct for effects of multiple hypothesis testing, resulting in p-value cutoffs in the range of 0.03-0.06. For each differentially expressed microRNA we calculated the fold-difference (ratio of the median normalized fluorescence) and the area under curve (AUC) of the response operating characteristic (ROC) curve. For classification, two microRNAs with opposite specificity were chosen at each decision point (FIG. 4), and their ratio of expression (ratio of the normalized fluorescence signal) was calculated for each sample. A threshold level for the value of the ratios was determined using the training set of samples (indicated by the grey shaded regions in FIG. 4BCD) by choosing the cutoff value with the smallest number of classification errors on the training set. These thresholds were used to classify the test samples.

7. RT-PCR

RNA was incubated in the presence of poly (A) polymerase (Poly (A) Polymerase NEB-M0276L), $MnCl_2$, and ATP for 1 hour at 37° C. Then, using an oligodT primer harboring a consensus sequence, reverse transcription was performed on total RNA using the reverse transcriptase SUPERSCRIPT® II RT (Invitrogen, Carlsbad, Calif.). Next, the cDNA was amplified by RT-PCR; this reaction contained a microRNA-specific forward primer, a TAQMAN® (MGB) probe complementary to the 3' of the specific microRNA sequence as well as to part of the polyA adaptor sequence, and a universal reverse primer complementary to the consensus 3' sequence of the oligodT tail.

The cycle threshold ($C_T$, the PCR cycle at which probe signal reaches the threshold) was determined for each microRNA. To allow comparison with results from the microarray, each value received was subtracted from 50. This 50-$C_T$ expression for each microRNA for each patient was compared with the signal obtained by the microarray method.

Example 1

Specific microRNAs are Differentially Expressed Between Different Histological Subtypes of Kidney Tumors 127 formalin-fixed, paraffin-embedded (FFPE) samples of renal tumors were collected, including 40 oncocytoma samples, 27 chromophobe samples, 34 conventional (clear) cell samples, and 26 papillary tumor samples. The initial sample set used for biomarker identification and for training a classifier included 71 samples. Total RNA was extracted from these samples, and microRNA expression was profiled using microarrays.

Figure 1:
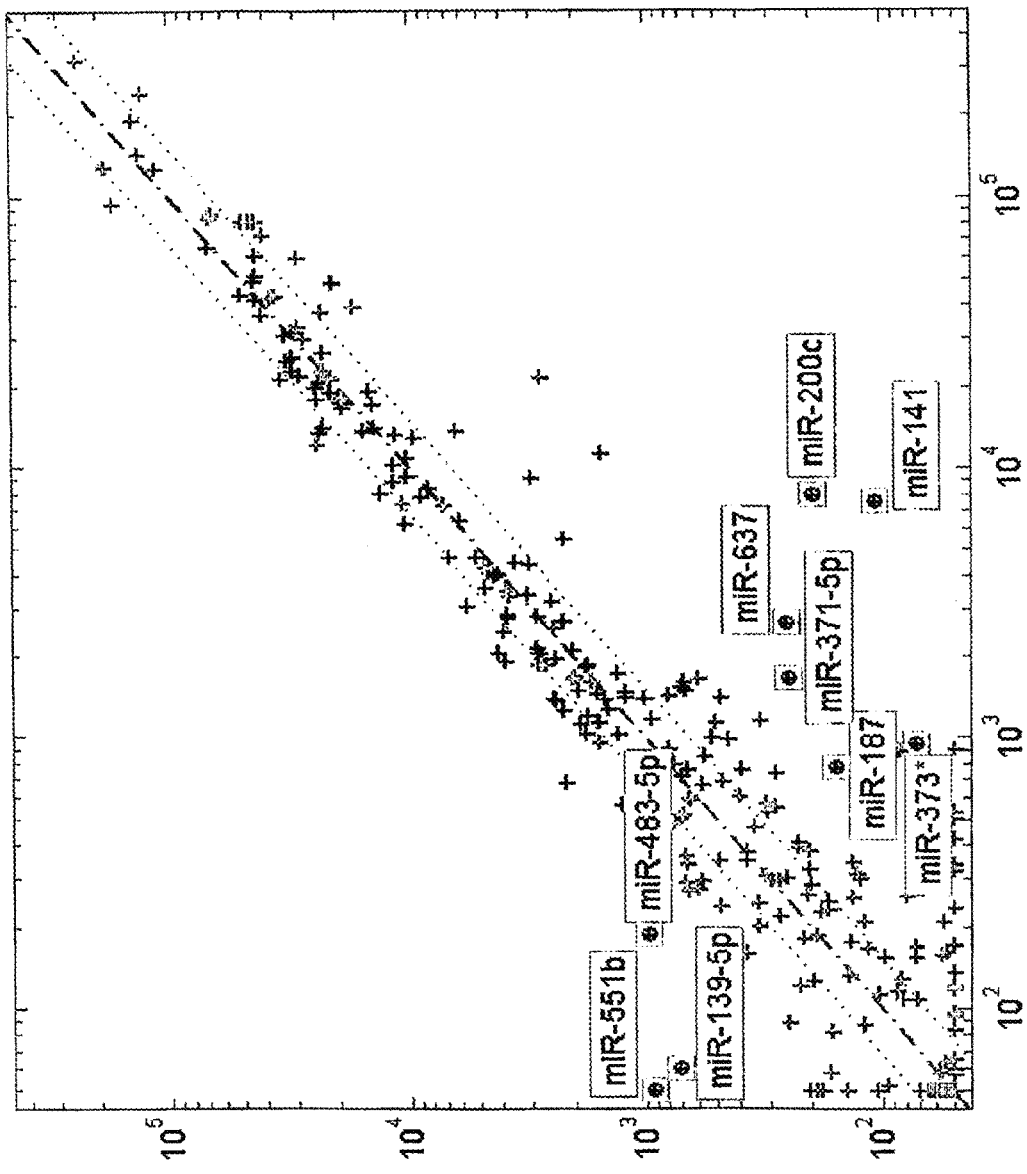
FIG. 1 is a Scatter-plot comparison of oncocytoma and chromophobe samples from the training set. Median normalized fluorescence of oncocytoma samples (n=21) (Y axis) is plotted against the median normalized fluorescence of chromophobe samples (n=13) (X axis). Each microRNA is represented by a black cross. Control probes and microRNAs that did not pass the minimum expression threshold of (median normalized fluorescence>700 in at least one of the two groups) are shown in grey. Diagonal line shows equal signals (dash-dot line) and 2-fold change in either direction (dotted lines). MicroRNAs that had a fold change greater than 4 in either direction and had a p-value lower than 0.0417 (the threshold determined for a False Discovery Rate of 0.1 or lower) are highlighted in circles.
Figure 2:
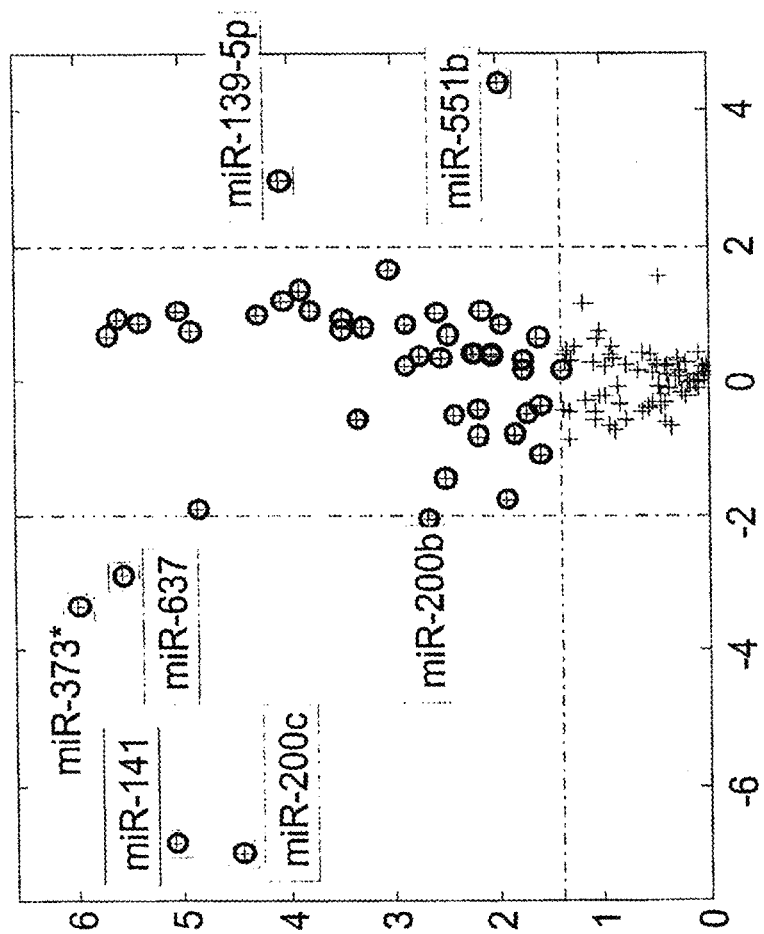
FIG. 2 is a Volcano plot showing the −log 10 (p-value) against the log 2 of the ratio of the median expression, for the same data of FIG. 1. MicroRNAs with strong fold-changes have a large absolute value of the log 2 (ratio). Vertical lines indicate 4-fold change in median signal in either direction; horizontal line indicates the p-value cutoff of 0.0417.
Figure 3A:
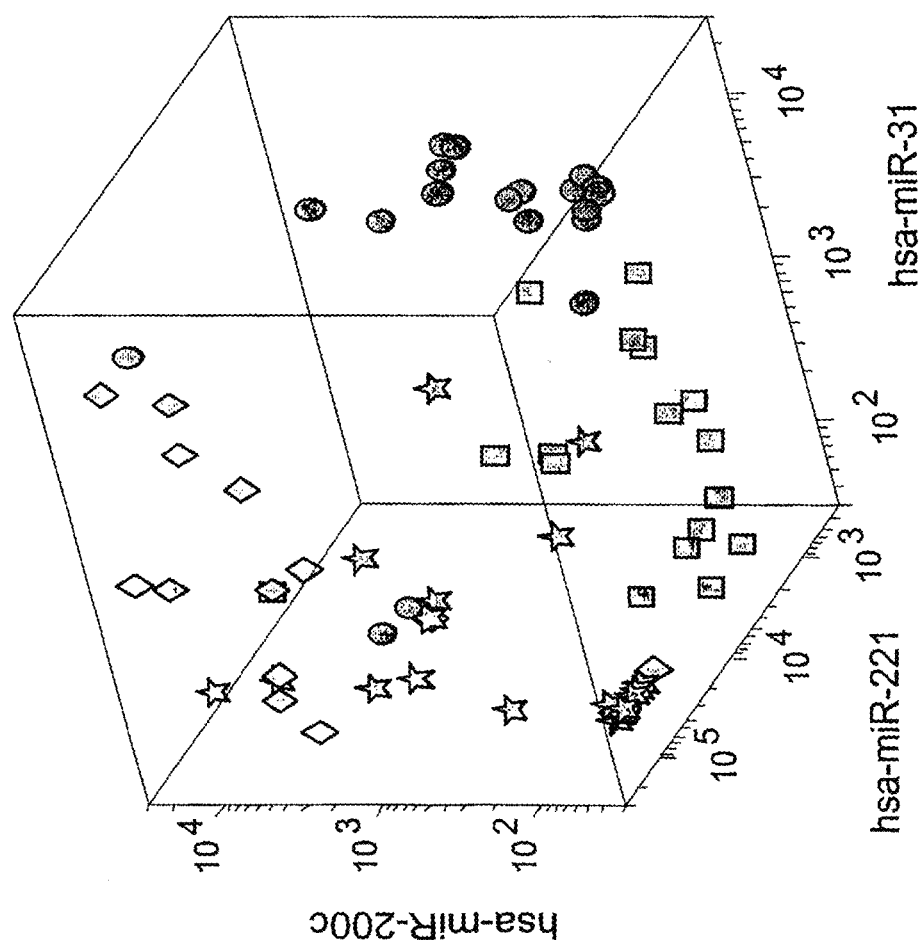
Figure 3B:
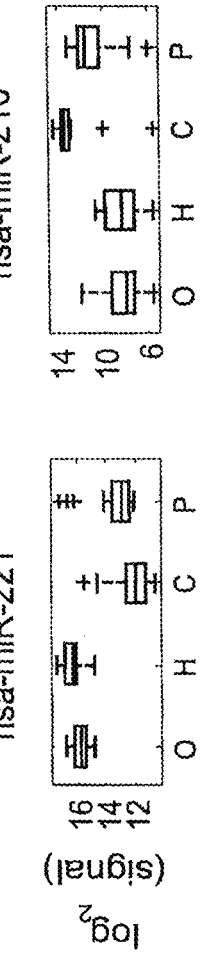
Figure 3C:
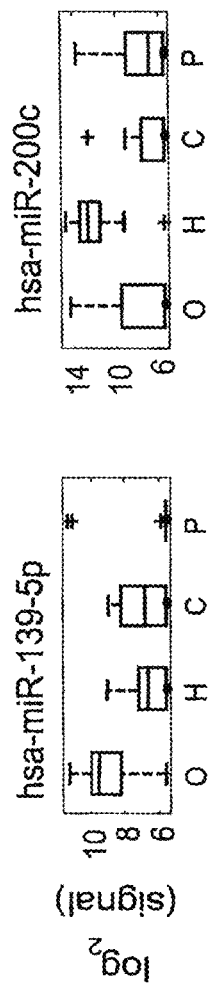
Figure 3D:
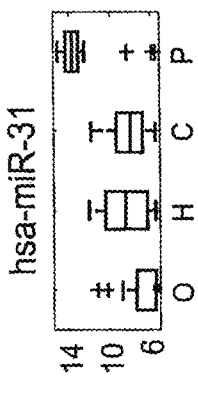
Figure 3D:
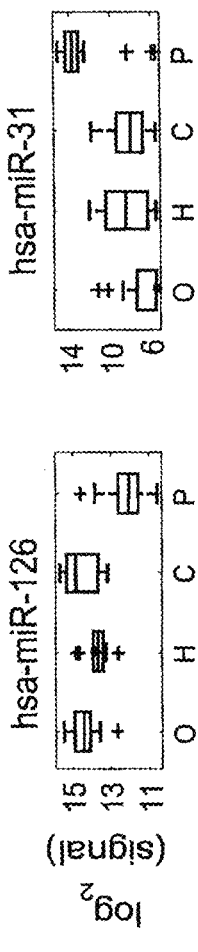

We first looked for microRNAs that are differentially expressed between different histological subtypes of kidney tumors. We compared the expression of microRNAs between oncocytoma samples (n=21), chromophobe tumors (n=13), conventional cell tumors (n=17), and papillary tumors (n=20). More than 900 microRNAs were compared using statistical tests. MicroRNAs were considered differentially expressed between any two histological types if their t-test significance (p-value) indicated a False Discovery Rate (FDR) below 0.1 and their median expression level changed at least 4-fold between the two groups (FIGS. 1-2). 33 microRNAs were identified as differentially expressed between different kidney tumors types (Table 2). To identify underlying similarities between the histological types, the expression level of these 33 microRNAs was used to cluster the 71 samples. This analysis identified four main clusters that closely followed the predefined groups. Further, the expression of microRNAs showed a high degree of similarity between conventional cell and papillary tumors, and between chromophobe and oncocytoma, and a lower degree of similarity between these pairs.

The clustering also identified groups of microRNAs with similar profiles. Such co-regulated groups can hint to a possible effect of upstream regulatory components. An analysis of predicted binding sites of transcription factors near the start sites of co-regulated microRNA transcripts generates a list of transcription factors that may be enriched for factors related to biological differences between the histological types (Table 3).

Given the underlying biological similarities between the tumor types, we decided to construct a classifier to identify kidney tumor subtype in two steps, following the binary structure of the hierarchical clustering tree: the first step identifies whether the sample belongs to one pair of types (chromophobe, oncocytoma) or to the other pair (conventional cell, papillary); the second step decides between the two types in each pair. The classifier therefore has three decision points, corresponding to the comparisons in Table 2. For each such decision point (or "node"), we chose two microRNAs: one that is highly expressed in one group, and another that is more strongly expressed in the other group. MicroRNAs were selected based on their expression levels and distributions in the training set (Table 2), with the aim of selecting microRNAs that provide a distinct difference in expression that can be used for accurate classification. For identifying between the pair of types (chromophobe, oncocytoma) and the pair (conventional cell, papillary), we chose hsa-miR-221 (SEQ ID NO: 25) and hsa-miR-210 (SEQ ID NO: 20); for identifying between chromophobe and oncocytoma, we chose hsa-miR-200c (SEQ ID NO: 34) and hsa-miR-139-5p (SEQ ID NO: 14); and for identifying between papillary and conventional cell, we chose hsa-miR-31 (SEQ ID NO: 4) and hsa-miR-126 (SEQ ID NO: 41) (FIG. 3). Using one microRNA from each set is sufficient to obtain a clear separation between the four groups (FIG. 3A), but to ensure better performance we used a combination of two microRNAs at each point. Amongst this set of microRNAs, each histological type has high expression of at least two microRNAs (e.g., hsa-miR-210 and hsa-miR-31 for papillary, or hsa-miR-221 and hsa-miR-200c for chromophobe), and low expression of at least two other microRNAs (FIG. 3).

We used the 71 samples of the training set to train a simple classifier, comprised of two steps and three pairs of microRNAs (FIG. 4). For each pair of microRNAs, a threshold was determined on the ratio of the expression levels of the two microRNAs (Methods)—this is equivalent to a straight line that separates two regions in log-space (see FIG. 4). In the first step (FIG. 4B), if the ratio of relative expression (normalized fluorescence) of hsa-miR-221 to relative expression (normalized fluorescence) of hsa-miR-210 is greater than the threshold value of 9.86, the sample takes the left branch (FIG. 4A) and is identified as either oncocytoma or chromophobe. If (hsa-miR-221/hsa-miR-210)<9.86, the samples takes the right branch (grey shaded region in FIG. 4B) and is identified as either conventional cell or papillary. In the second step, the same process is used—if (hsa-miR-200c/hsa-miR-139-5p) >33.1, the sample is classified as chromophobe (grey region in FIG. 4C), otherwise it is classified as oncocytoma. Alternatively, if (hsa-miR-126/hsa-miR-31)<2.32, the sample is classified as papillary (grey region in FIG. 4D), otherwise it is classified as conventional cell. In the training set, this classifier correctly identified 62 out of 71 samples, with an overall accuracy of 87% (95% confidence interval: 77%-94%, assuming a binomial distribution).

56 additional samples were collected as an independent test set (FIG. 4). These samples were processed and their microRNA expression profiles were measured using the same protocols, more than two months after the initial training set samples were profiled. The microRNA expression profiles of these samples were used to predict their histological subtype according to the classification algorithm defined above (FIG. 4). Of the 56 test samples, 52 samples were classified correctly and four samples were classified incorrectly: two of the 14 chromophobe samples were classified as oncocytoma; one of the 19 oncocytoma samples was classified as chromophobe; one of the 17 conventional cell sample was classified as oncocytoma; and all 6 papillary samples were classified correctly. Identification sensitivity was 95% for oncocytoma, 86% for chromophobe, 94% for conventional cell, and 100% for papillary, with overall accuracy of 93% (95% confidence interval: 83%-98%, assuming a binomial distribution).

TABLE 2

Differentially expressed microRNAs

| Micro RNA name | Median values Oncocytoma | Chromophobe | Conventional | Papillary | (Conventional Cell + Papillary) vs. (Oncocytoma + Chromophobe) | | | Chromophobe vs. Oncocytoma | | | Papillary vs. Conventional Cell | | |
|---|---|---|---|---|---|---|---|---|---|---|---|---|---|
| | | | | | p-value | fold | AUC | p-value | fold | AUC | p-value | fold | AUC |
| hsa-miR-141 | 50 | 5800 | 50 | 72 | 1.3E−03 | 14.38 | 0.67 | 8.0E−06 | 116.81 | 0.88 | 2.5E−01 | 1.45 | 0.64 |
| hsa-miR-200c | 50 | 6500 | 50 | 130 | 2.7E−03 | 11.84 | 0.68 | 3.5E−05 | 129.68 | 0.88 | 1.3E−01 | 2.61 | 0.66 |
| hsa-miR-373* | 72 | 730 | 84 | 79 | 2.7E−03 | 2.64 | 0.67 | 1.0E−06 | 10.23 | 0.92 | 5.6E−01 | 1.06 | 0.54 |
| hsa-miR-637 | 350 | 2700 | 200 | 350 | 1.0E−03 | 2.25 | 0.71 | 2.7E−06 | 7.56 | 0.92 | 1.7E−01 | 1.76 | 0.65 |
| hsa-miR-371-5p | 420 | 1600 | 220 | 300 | 5.2E−04 | 2.26 | 0.75 | 1.4E−05 | 3.73 | 0.91 | 1.4E−01 | 1.36 | 0.66 |
| hsa-miR-557 | 390 | 1100 | 150 | 210 | 6.3E−06 | 3.66 | 0.79 | 3.2E−03 | 2.72 | 0.79 | 3.0E−01 | 1.39 | 0.61 |
| hsa-miR-193b | 3900 | 1800 | 1200 | 670 | 2.6E−05 | 3.2 | 0.8 | 6.8E−02 | 2.2 | 0.68 | 3.0E−01 | 1.74 | 0.6 |
| hsa-miR-365 | 2700 | 890 | 830 | 500 | 2.6E−04 | 2.49 | 0.78 | 9.2E−04 | 3.08 | 0.81 | 2.6E−02 | 1.67 | 0.7 |
| hsa-miR-126 | 21000 | 14000 | 29000 | 4200 | 4.9E−03 | 1.68 | 0.66 | 3.3E−03 | 1.57 | 0.81 | 5.0E−09 | 6.81 | 0.95 |
| hsa-miR-139-5p | 790 | 100 | 120 | 50 | 2.7E−04 | 6.81 | 0.76 | 8.6E−05 | 7.75 | 0.87 | 1.6E−01 | 2.38 | 0.73 |
| hsa-miR-222 | 52000 | 73000 | 5200 | 7500 | 4.1E−15 | 8.24 | 0.92 | 3.8E−03 | 1.42 | 0.74 | 6.3E−02 | 1.45 | 0.74 |
| hsa-miR-221 | 58000 | 81000 | 4000 | 8000 | 4.4E−17 | 10.95 | 0.93 | 1.9E−02 | 1.39 | 0.74 | 1.1E−02 | 2 | 0.81 |
| hsa-miR-221* | 800 | 630 | 50 | 50 | 1.1E−17 | 14.39 | 0.94 | 1.3E−01 | 1.27 | 0.69 | 1.1E−01 | 1 | 0.6 |

TABLE 2-continued

Differentially expressed microRNAs

| Micro RNA name | Median values Oncocytoma | Chromophobe | Conventional | Papillary | (Conventional Cell + Papillary) vs. (Oncocytoma + Chromophobe) | | | Chromophobe vs. Oncocytoma | | | Papillary vs. Conventional Cell | | |
|---|---|---|---|---|---|---|---|---|---|---|---|---|---|
| | | | | | p-value | fold | AUC | p-value | fold | AUC | p-value | fold | AUC |
| hsa-miR-10a | 37000 | 24000 | 6100 | 14000 | 9.0E−07 | 4.16 | 0.86 | 9.2E−02 | 1.53 | 0.73 | 5.7E−03 | 2.24 | 0.84 |
| hsa-miR-30b | 45000 | 59000 | 13000 | 19000 | 5.1E−11 | 2.69 | 0.9 | 2.8E−01 | 1.32 | 0.63 | 5.2E−03 | 1.5 | 0.76 |
| hsa-miR-182 | 1400 | 1500 | 50 | 580 | 1.1E−06 | 5.8 | 0.81 | 8.1E−01 | 1.03 | 0.55 | 5.0E−04 | 11.66 | 0.81 |
| hsa-miR-187 | 400 | 720 | 50 | 50 | 4.3E−06 | 9.13 | 0.81 | 4.9E−02 | 1.82 | 0.68 | 9.5E−01 | 1 | 0.51 |
| hsa-miR-551b | 1100 | 50 | 50 | 1300 | 2.8E−01 | 5.31 | 0.56 | 1.1E−02 | 21.1 | 0.75 | 2.1E−06 | 25.16 | 0.86 |
| hsa-miR-138 | 50 | 50 | 70 | 790 | 3.9E−04 | 8.42 | 0.75 | 4.8E−01 | 1 | 0.6 | 1.7E−04 | 11.27 | 0.83 |
| hsa-miR-31 | 50 | 330 | 250 | 14000 | 2.5E−06 | 29.31 | 0.81 | 1.5E−02 | 6.63 | 0.73 | 2.5E−06 | 56.37 | 0.89 |
| hsa-miR-196b | 430 | 210 | 370 | 1100 | 9.1E−02 | 1.53 | 0.63 | 4.1E−01 | 2.05 | 0.58 | 7.0E−02 | 2.81 | 0.72 |
| hsa-miR-200a | 1600 | 5500 | 3200 | 11000 | 3.5E−02 | 1.74 | 0.66 | 1.2E−02 | 3.38 | 0.82 | 8.0E−04 | 3.44 | 0.9 |
| hsa-miR-200b | 2000 | 8200 | 2800 | 15000 | 9.5E−02 | 1.85 | 0.63 | 2.2E−03 | 4.13 | 0.81 | 3.3E−05 | 5.17 | 0.91 |
| hsa-miR-192 | 50 | 220 | 5200 | 1600 | 4.6E−08 | 21.24 | 0.84 | 5.4E−01 | 4.44 | 0.61 | 6.5E−02 | 3.28 | 0.74 |
| hsa-miR-194 | 58 | 160 | 4200 | 2300 | 1.2E−07 | 20.63 | 0.83 | 4.2E−01 | 2.69 | 0.62 | 2.1E−01 | 1.87 | 0.69 |
| hsa-miR-455-3p | 120 | 98 | 1500 | 1200 | 1.8E−13 | 11.42 | 0.92 | 2.3E−01 | 1.27 | 0.58 | 2.0E−01 | 1.27 | 0.63 |
| hsa-miR-146a | 350 | 310 | 1400 | 1900 | 3.4E−12 | 4.98 | 0.92 | 7.0E−01 | 1.13 | 0.55 | 2.8E−01 | 1.38 | 0.64 |
| hsa-miR-204 | 50 | 50 | 1700 | 2700 | 5.1E−10 | 48.33 | 0.87 | 9.9E−01 | 1 | 0.53 | 4.9E−02 | 1.59 | 0.71 |
| hsa-miR-210 | 280 | 370 | 11000 | 3300 | 1.2E−10 | 15.79 | 0.89 | 9.2E−01 | 1.32 | 0.52 | 8.4E−03 | 3.38 | 0.89 |
| hsa-miR-21 | 20000 | 21000 | 110000 | 180000 | 2.7E−10 | 7.79 | 0.88 | 4.4E−01 | 1.06 | 0.56 | 1.2E−01 | 1.56 | 0.68 |
| hsa-miR-21* | 50 | 66 | 800 | 2000 | 1.4E−12 | 28.66 | 0.91 | 4.3E−01 | 1.32 | 0.63 | 6.9E−02 | 2.45 | 0.78 |
| hsa-miR 146b-5p | 77 | 160 | 1700 | 1200 | 6.5E−12 | 10.4 | 0.9 | 5.0E−01 | 2.01 | 0.55 | 3.7E−01 | 1.38 | 0.58 |
| hsa-miR-155 | 77 | 83 | 1300 | 600 | 9.2E−09 | 9.65 | 0.85 | 9.5E−01 | 1.08 | 0.5 | 5.4E−02 | 2.23 | 0.72 |

Pair-wise comparisons of each of the four histological types identified 33 differentially expressed microRNAs. Here we show the p-value, fold-change of the median signal, and area under the ROC curve (AUC) for each of these microRNAs in comparing papillary to conventional cell tumors, oncocytomas to chromophobe tumors, and in comparing the combination of conventional cell with papillary to the union of chromophobe with oncocytoma.

TABLE 3

Association between co-expressed microRNAs and their predicted co-regulating transcription factors (TFs)

| Transcription Factor(s) | MicroRNAs with predicted TF binding sites |
|---|---|
| *microRNAs upregulated in Oncocytoma* | |
| Ahr, Arnt, GR-alpha, GR-beta | hsa-miR-139-5p, hsa-miR-365 |
| *microRNAs upregulated in Oncocytoma and chromophobe tumors* | |
| AR, Arnt, MEF-2A, NCX | hsa-miR-10a and hsa-miR-221/222 |
| Cdc5, POU3F2 (N-Oct-5a), POU3F2 (N-Oct-5b) | hsa-miR-182, hsa-miR-221/222 |
| c-Myc, Max1, SREBP-1a (b, c) | hsa-miR-10a, hsa-miR-30b |
| E4BP4, Hlf | hsa-miR-221/222, hsa-miR-30b |
| GATA-1, MZF-1 | hsa-miR-10a, hsa-miR-182 |
| LCR-F1 | hsa-miR-182, hsa-miR-221/222, hsa-miR-30b |
| POU3F2, TBP | hsa-miR-10a, hsa-miR-182, hsa-miR-221/222 |
| *microRNAs upregulated in papillary tumors* | |
| AREB6 | hsa-miR-196b, hsa-miR-200a/b, hsa-miR-31 |
| C/EBPbeta | hsa-miR-196b, hsa-miR-31 |
| HNF-1A | hsa-miR-200a/b, hsa-miR-31 |
| POU2F1, Sp1, SRF, YY1 | hsa-miR-196b, hsa-miR-200a/b |
| *microRNAs upregulated in conventional cell and papillary tumors* | |
| AhR, AP-4, Arnt | hsa-miR-192/4, hsa-miR-210, hsa-miR-455-3p |
| AP-2alphaA, AP-2gamma | hsa-miR-21, hsa-miR-210, hsa-miR-455-3p |
| AR, AREB6, Nkx2-1 | hsa-miR-192/4, hsa-miR-204 |
| ATF6 | hsa-miR-192/4, hsa-miR-455-3p |
| E47 | hsa-miR-192/4, hsa-miR-204, hsa-miR-455-3p |
| Elk-1 | hsa-miR-204, hsa-miR-21 |
| AP-2rep, FOXD1, MAZR | hsa-miR-204, hsa-miR-210 |
| GATA-1, NF-kappaB2, Sox9 | hsa-miR-146a, hsa-miR-204 |
| GR-alpha | hsa-miR-210, hsa-miR-455-3p |
| HSF1 (long), Meis-1 | hsa-miR-146a, hsa-miR-204, hsa-miR-210 |
| HSF2, OCA-B, Octa-factor, octamer-binding factor, Oct-B1(B2, B3), POU2F2 (2F2B, 2F2C, 3F1, 3F2, 4F1(1), 5F1A, 5F1B, 5F1C) | hsa-miR-146a, hsa-miR-210 |
| ISGF-3, Pax-5, STAT1alpha, STAT1beta, STAT3 | hsa-miR-204, hsa-miR-455-3p |
| MEF-2A | hsa-miR-146a, hsa-miR-21, hsa-miR-455-3p |
| NF-kappaB, NF-kappaB1 | hsa-miR-146a, hsa-miR-192/4, hsa-miR-204, hsa-miR-455-3p |
| Pax-2 | hsa-miR-192/4, hsa-miR-204, hsa-miR-210, hsa-miR-455-3p |
| POU2F1 | hsa-miR-146a, hsa-miR-192/4, hsa-miR-204, hsa-miR-210 |
| PPAR-gamma1, PPAR-gamma2 | hsa-miR-192/4, hsa-miR-204, hsa-miR-210 |
| RelA | hsa-miR-146a, hsa-miR-192/4, hsa-miR-455-3p | microRNAs were clustered according to a similar expression pattern across the 4 different renal tumor types as described above. TFs were associated to microRNAs following existence of predicted TF binding sites in the microRNA promoter. The table lists only TFs which were associated to at least 2 co-expressed microRNAs. Several TFs in the same row indicate that all TFs are associated to the same microRNAs in that row. microRNAs presented as hsa-miR-###/# (e.g hsa-miR-192/4), indicate that the 2 microRNAs are located in the same genomic cluster and therefore are predicted to be part of a shared pri-microRNA.

Example 2

Specific microRNAs are Able to Distinguish Between Oncocytoma Renal Tumor Samples and Chromophobe RCC Samples The analysis of the microarray results of oncocytoma renal tumor samples versus chromophobe RCC samples are presented in Table 4. The results exhibited a significant difference in the expression pattern of several miRs. The normalized expression levels of hsa-miR-141 (SEQ ID NO: 32) and hsa-miR-200c (SEQ ID NO: 34) were found to be higher in chromophobe RCC samples in comparison to oncocytoma renal tumor samples. The normalized expression levels of hsa-miR-140-5p (SEQ ID NO: 28), hsa-miR-139-5p (SEQ ID NO: 14) and hsa-miR-551b (SEQ ID NO: 30) were found to be higher in oncocytoma renal tumor samples in comparison to chromophobe RCC samples.

TABLE 4

| miR name | miR SEQ ID No | Hairpin SEQ ID NO. | p-value | fold-change | median values group 1 | median values group 2 |
|---|---|---|---|---|---|---|
| Up regulated in chromophobe RCC: | | | | | | |
| hsa-miR-141 | 32 | 33 | 6.60E−05 | 152.26 | 7.60E+03 | 5.00E+01 |

TABLE 4-continued

| miR name | miR SEQ ID No | Hairpin SEQ ID NO. | p-value | fold-change | median values group 1 | median values group 2 |
|---|---|---|---|---|---|---|
| hsa-miR-200c | 34 | 35 | 2.10E−04 | 99.52 | 8.00E+03 | 8.00E+01 |
| Down regulated in chromophobe RCC: | | | | | | |
| hsa-miR-551b | 30 | 31 | 2.10E−02 | 18.86 | 5.50E+01 | 1.00E+03 |
| hsa-miR-139-5p | 14 | 15 | 1.60E−04 | 10.09 | 8.10E+01 | 8.10E+02 |
| hsa-miR-140-5p | 28 | 29 | 8.20E−05 | 8.25 | 6.20E+01 | 5.10E+02 | miR name: is the miRBase registry name (release 10)
p-value: is the result of unpaired two-sided t-test between the two groups of samples
These miRs can be used to distinguish between oncocytoma renal tumor and chromophobe RCC. The classification could be conducted either with a simple threshold (1 or 2 dimension threshold), a logistic regression model or any other classifier.

TABLE 5

| miR name | miR SEQ ID No | Hairpin SEQ ID NO. | p-value | fold-change | median values group 1 | median values group 2 |
|---|---|---|---|---|---|---|
| Up regulated in clear cell RCC: | | | | | | |
| hsa-miR-192 | 6 | 7 | 1.30E−05 | 109.55 | 6.30E+03 | 5.70E+01 |
| hsa-miR-194 | 1 | 2, 3 | 2.70E−05 | 78.06 | 5.10E+03 | 6.60E+01 |
| hsa-miR-210 | 20 | 21 | 2.30E−07 | 37.8 | 1.20E+04 | 3.30E+02 |
| hsa-miR-146b-5p | 16 | 17 | 2.60E−09 | 19.83 | 1.90E+03 | 9.70E+01 |
| hsa-miR-155 | 22 | 23 | 5.10E−07 | 18.06 | 1.40E+03 | 8.00E+01 |
| hsa-miR-455-3p | 24 | 49 | 1.90E−05 | 8.43 | 1.30E+03 | 1.50E+02 |
| hsa-miR-21 | 47 | 11 | 1.70E−06 | 6.05 | 1.40E+05 | 2.30E+04 |
| Down regulated in clear cell RCC: | | | | | | |
| hsa-miR-182 | 36 | 37 | 2.20E−07 | 33.65 | 5.00E+01 | 1.70E+03 |
| hsa-miR-551b | 30 | 31 | 1.90E−05 | 23.48 | 5.00E+01 | 1.20E+03 |
| hsa-miR-221 | 25 | 13 | 4.00E−10 | 11.81 | 6.50E+03 | 7.70E+04 |
| hsa-miR-222 | 26 | 27 | 3.20E−09 | 8.01 | 7.70E+03 | 6.20E+04 |
| hsa-miR-10a | 48 | 19 | 3.00E−07 | 5.79 | 7.50E+03 | 4.30E+04 |
| MID-00536 | 38 | 39, 40 | 1.20E−13 | 5.49 | 5.20E+03 | 2.80E+04 |

Example 3

Specific microRNAs are Able to Distinguish Between Oncocytoma Renal Tumor Samples and Clear Cell RCC Samples The analysis of the microarray results of oncocytoma renal tumor samples versus clear cell RCC samples are presented in Table 5. The results exhibited a significant difference in the expression pattern of several miRs. The normalized expression levels of hsa-miR-551b (SEQ ID NO: 30), hsa-miR-182 (SEQ ID NO: 36), hsa-miR-221 (SEQ ID NO: 25), hsa-miR-222 (SEQ ID NO: 26), hsa-miR-10a (SEQ ID NO: 48) and MID-00536 (SEQ ID NO: 38) were found to be higher in oncocytoma renal tumor samples in comparison to clear cell RCC samples. The normalized expression levels of hsa-miR-21 (SEQ ID NO: 47), hsa-miR-210 (SEQ ID NO: 20), hsa-miR-192 (SEQ ID NO: 6), hsa-miR-194 (SEQ ID NO: 1), hsa-miR-146b-5p (SEQ ID NO: 16), hsa-miR-155 (SEQ ID NO: 22) and hsa-miR-455-3p (SEQ ID NO: 24) were found to be higher in clear cell RCC samples in comparison to oncocytoma renal tumor samples.

Example 4

Specific microRNAs are Able to Distinguish Between Benign Renal Tumor Samples and Malignant RCC Samples The analysis of the microarray results of benign renal tumor samples versus malignant RCC samples are presented in Table 6. The results exhibited a significant difference in the expression pattern of several miRs. The normalized expression levels of hsa-miR-221 (SEQ ID NO: 25), hsa-miR-222 (SEQ ID NO: 26), hsa-miR-10a* (SEQ ID NO: 18), hsa-miR-139-5p (SEQ ID NO: 14) and hsa-miR-221* (SEQ ID NO: 12) were found to be higher in benign renal tumor samples in comparison to malignant RCC samples. The normalized expression levels of hsa-miR-21 (SEQ ID NO: 47), hsa-miR-21* (SEQ ID NO: 10), hsa-miR-210 (SEQ ID NO: 20), hsa-miR-192 (SEQ ID NO: 6), hsa-miR-194 (SEQ ID NO: 1), hsa-miR-146b-5p (SEQ ID NO: 16), hsa-miR-204 (SEQ ID NO: 8), hsa-miR-31 (SEQ ID NO: 4), hsa-miR-155 (SEQ ID NO: 22) and hsa-miR-455-3p (SEQ ID NO: 24) were found to be higher in malignant RCC samples in comparison to benign RCC samples.

TABLE 6

| miR name | miR SEQ ID No | Hairpin SEQ ID NO. | p-value | fold-change | median values group 1 | median values group 2 |
|---|---|---|---|---|---|---|
| Up regulated in malignant RCC: | | | | | | |
| hsa-miR-194 | 1 | 2, 3 | 1.10E−04 | 35.54 | 2.20E+03 | 6.30E+01 |
| hsa-miR-31 | 4 | 5 | 2.80E−05 | 30.95 | 1.50E+03 | 5.00E+01 |
| hsa-miR-192 | 6 | 7 | 1.20E−04 | 30.17 | 1.70E+03 | 5.50E+01 |
| hsa-miR-204 | 8 | 9 | 5.00E−04 | 27.22 | 1.40E+03 | 5.00E+01 |
| hsa-miR-21* | 10 | 11 | 2.20E−07 | 18.62 | 9.30E+02 | 5.00E+01 |
| hsa-miR-146b-5p | 16 | 17 | 8.10E−07 | 14.17 | 1.20E+03 | 8.50E+01 |
| hsa-miR-210 | 20 | 21 | 1.70E−05 | 11.86 | 3.80E+03 | 3.20E+02 |
| hsa-miR-155 | 22 | 23 | 8.70E−05 | 8.84 | 7.00E+02 | 7.90E+01 |
| hsa-miR-455-3p | 24 | 49 | 1.40E−04 | 6.58 | 9.80E+02 | 1.50E+02 |
| hsa-miR-21 | 47 | 11 | 2.30E−06 | 6.55 | 1.40E+05 | 2.10E+04 |

TABLE 6-continued

| miR name | miR SEQ ID No | Hairpin SEQ ID NO. | p-value | fold-change | median values group 1 | median values group 2 |
|---|---|---|---|---|---|---|
| Down regulated in malignant RCC: | | | | | | |
| hsa-miR-221* | 12 | 13 | 8.90E−11 | 18 | 5.00E+01 | 9.00E+02 |
| hsa-miR-139-5p | 14 | 15 | 2.20E−09 | 15.9 | 5.30E+01 | 8.40E+02 |
| hsa-miR-10a* | 18 | 19 | 2.00E−10 | 12.89 | 5.00E+01 | 6.40E+02 |
| hsa-miR-221 | 25 | 13 | 6.70E−07 | 7.82 | 8.90E+03 | 7.00E+04 |
| hsa-miR-222 | 26 | 27 | 1.00E−05 | 5.87 | 9.20E+03 | 5.40E+04 |

Example 5

Specific microRNAs are Able to Distinguish Between Clear Cell RCC Samples and Chromophobe RCC Samples The analysis of the microarray results of clear cell RCC samples versus chromophobe RCC samples exhibited a significant difference in the expression pattern of several miRs, as indicated in Table 7. The normalized expression levels of hsa-miR-192 (SEQ ID NO: 6), hsa-miR-194 (SEQ ID NO: 1) and hsa-miR-155 (SEQ ID NO: 22) were found to be higher in clear cell RCC samples in comparison to chromophobe RCC samples. The normalized expression levels of hsa-miR-141 (SEQ ID NO: 32) and hsa-miR-200c (SEQ ID NO: 34) hsa-miR-182 (SEQ ID NO: 36) and hsa-miR-187 (SEQ ID NO: 43) were found to be higher in chromophobe RCC samples in comparison to clear cell RCC samples.

TABLE 7

| miR name | miR SEQ ID No | Hairpin SEQ ID NO. | p-value | fold-change | median values group 1 | median values group 2 |
|---|---|---|---|---|---|---|
| Up regulated in clear cell RCC: | | | | | | |
| hsa-miR-192 | 6 | 7 | 6.30E−04 | 29.54 | 5.80E+03 | 2.00E+02 |
| hsa-miR-194 | 1 | 2, 3 | 1.60E−03 | 29.24 | 4.90E+03 | 1.70E+02 |
| hsa-miR-155 | 22 | 23 | 2.30E−05 | 22.84 | 1.50E+03 | 6.60E+01 |
| Down regulated in clear cell RCC: | | | | | | |
| hsa-miR-200c | 34 | 35 | 2.00E−06 | 181.94 | 5.00E+01 | 9.10E+03 |
| hsa-miR-141 | 32 | 33 | 1.20E−06 | 175.15 | 5.00E+01 | 8.80E+03 |
| hsa-miR-182 | 36 | 37 | 3.00E−05 | 36.53 | 5.00E+01 | 1.80E+03 |
| hsa-miR-187 | 43 | 44 | 3.20E−05 | 30.91 | 5.00E+01 | 1.50E+03 |

Example 6

Specific microRNAs are Able to Distinguish Between Clear Cell RCC Samples and Papillary RCC Samples The analysis of the microarray results of clear cell RCC samples versus papillary RCC samples exhibited a significant difference in the expression pattern of several miRs, as indicated in Table 8. The normalized expression levels of hsa-miR-126 (SEQ ID NO: 41) were found to be higher in clear cell RCC samples in comparison to papillary RCC samples. The normalized expression levels of hsa-miR-31 (SEQ ID NO: 4), hsa-miR-551b (SEQ ID NO: 30), hsa-miR-138 (SEQ ID NO: 50) and hsa-miR-204 (SEQ ID NO: 8) were found to be higher in papillary RCC samples in comparison to clear cell RCC samples.

TABLE 8

| miR name | miR SEQ ID No | Hairpin SEQ ID NO | p-value | fold-change | median values group 1 | median values group 2 |
|---|---|---|---|---|---|---|
| Up regulated in clear cell RCC samples: | | | | | | |
| hsa-miR-126 | 41 | 42 | 3.50E−11 | 5.35 | 2.60E+04 | 4.90E+03 |
| Down regulated in clear cell RCC samples: | | | | | | |
| hsa-miR-31 | 4 | 5 | 2.90E−06 | 38.42 | 4.50E+02 | 1.70E+04 |
| hsa-miR-551b | 30 | 31 | 6.60E−08 | 32.03 | 5.00E+01 | 1.60E+03 |
| hsa-miR-138 | 50 | 51 | 3.10E−06 | 17.04 | 5.70E+01 | 9.80E+02 |
| hsa-miR-204 | 8 | 9 | 8.20E−04 | 5.77 | 6.20E+02 | 3.60E+03 |

Example 7

Specific microRNAs are Able to Distinguish Between Chromophobe RCC Samples and Papillary RCC Samples The analysis of the microarray results of chromophobe RCC samples and papillary RCC samples exhibited a significant difference in the expression pattern of several miRs, as indicated in Table 9. The normalized expression levels of hsa-miR-141 (SEQ ID NO: 32) and hsa-miR-200c (SEQ ID NO: 34), hsa-miR-187 (SEQ ID NO: 43), hsa-miR-150* (SEQ ID NO: 52), hsa-miR-221 (SEQ ID NO: 25) and hsa-miR-222 (SEQ ID NO: 26) were found to be higher in chromophobe RCC samples in comparison to papillary RCC samples. The normalized expression levels of hsa-miR-204 (SEQ ID NO: 8), hsa-miR-31 (SEQ ID NO: 4), hsa-miR-21* (SEQ ID NO: 10), hsa-miR-551b (SEQ ID NO: 30), hsa-miR-21 (SEQ ID NO: 47), hsa-miR-194 (SEQ ID NO: 1) and hsa-miR-455-3p (SEQ ID NO: 24) were found to be higher in papillary RCC samples in comparison to chromophobe RCC samples.

TABLE 9

| miR name | miR SEQ ID NO. | Hairpin SEQ ID NO. | p-value | fold-change | median values group 1 | group 2 |
|---|---|---|---|---|---|---|
| Up regulated in chromophobe RCC: | | | | | | |
| hsa-miR-141 | 32 | 33 | 1.40E−07 | 132.72 | 7.50E+03 | 5.70E+01 |
| hsa-miR-200c | 34 | 35 | 3.80E−06 | 70.3 | 7.80E+03 | 1.10E+02 |
| hsa-miR-187 | 43 | 44 | 2.90E−07 | 24.59 | 1.20E+03 | 5.00E+01 |
| hsa-miR-150* | 52 | 53 | 1.00E−07 | 16.87 | 2.00E+03 | 1.20E+02 |
| hsa-miR-221 | 25 | 13 | 6.00E−10 | 11.13 | 8.60E+04 | 7.70E+03 |
| hsa-miR-222 | 26 | 27 | 3.20E−09 | 9.9 | 6.90E+04 | 6.90E+03 |
| Down regulated in chromophobe RCC: | | | | | | |
| hsa-miR-204 | 8 | 9 | 1.30E−07 | 49.96 | 5.40E+01 | 2.70E+03 |
| hsa-miR-31 | 4 | 5 | 2.40E−04 | 42.6 | 3.50E+02 | 1.50E+04 |
| hsa-miR-21* | 10 | 11 | 3.60E−08 | 38.3 | 6.10E+01 | 2.30E+03 |
| hsa-miR-551b | 30 | 31 | 2.10E−03 | 22.55 | 5.50E+01 | 1.30E+03 |
| hsa-miR-21 | 47 | 11 | 4.90E−09 | 16.3 | 1.80E+04 | 2.90E+05 |
| hsa-miR-194 | 1 | 2, 3 | 3.30E−03 | 14.36 | 1.50E+02 | 2.20E+03 |
| hsa-miR-455-3p | 24 | 49 | 2.90E−10 | 11.73 | 9.30E+01 | 1.10E+03 |

Example 8

Specific microRNAs are Able to Distinguish Between Oncocytoma Renal Tumor Samples and Papillary RCC Samples The analysis of the microarray results of oncocytoma renal tumor samples and papillary RCC samples exhibited a significant difference in the expression pattern of several miRs, as indicated in Table 10. The normalized expression levels of hsa-miR-221* (SEQ ID NO: 12), hsa-miR-221 (SEQ ID NO: 25), hsa-miR-222 (SEQ ID NO: 26) and hsa-miR-126 (SEQ ID NO: 41) were found to be higher in oncocytoma renal tumor samples in comparison to papillary RCC samples. The normalized expression levels of hsa-miR-31 (SEQ ID NO: 4), hsa-miR-204 (SEQ ID NO: 8), hsa-miR-21* (SEQ ID NO: 10), hsa-miR-21 (SEQ ID NO: 47) and hsa-miR-146a (SEQ ID NO: 45) were found to be higher in papillary RCC samples in comparison to oncocytoma renal tumor samples.

TABLE 10

| miR name | miR SEQ ID NO: | Hairpin SEQ ID NO: | p-value | fold-change | median values group 1 | group 2 |
|---|---|---|---|---|---|---|
| Up regulated in oncocytoma: | | | | | | |
| hsa-miR-221* | 12 | 13 | 7.50E−14 | 16.52 | 8.30E+02 | 5.00E+01 |
| hsa-miR-221 | 25 | 13 | 1.20E−14 | 9.21 | 7.70E+04 | 8.30E+03 |
| hsa-miR-222 | 26 | 27 | 2.70E−13 | 7.46 | 5.70E+04 | 7.60E+03 |
| hsa-miR-126 | 41 | 42 | 1.80E−12 | 5.47 | 2.40E+04 | 4.30E+03 |
| Down regulated in oncocytoma: | | | | | | |
| hsa-miR-31 | 4 | 5 | 1.10E−09 | 322.27 | 5.00E+01 | 1.60E+04 |
| hsa-miR-204 | 8 | 9 | 5.80E−10 | 61.41 | 5.00E+01 | 3.10E+03 |
| hsa-miR-21* | 10 | 11 | 1.30E−11 | 49.27 | 5.00E+01 | 2.50E+03 |
| hsa-miR-21 | 47 | 11 | 4.10E−09 | 9.84 | 2.10E+04 | 2.10E+05 |
| hsa-miR-146a | 45 | 46 | 2.00E−10 | 5.66 | 3.70E+02 | 2.10E+03 |

Example 9

PCR Validation of Differentially Expressed microRNAs Between Different Histological Subtypes of Kidney Tumors Of the 127 samples tested on the microarray, 32 formalin-fixed, paraffin-embedded (FFPE) samples of renal tumors were tested using qRT-PCR, including 8 oncocytoma samples, 8 chromophobe samples, 8 conventional (clear) cell samples, and 8 papillary tumor samples. The samples for qRT-PCR where randomly chosen within each group blinded to their microarray signals.

Correlation between microarray and qRT-PCR results was assessed using the tree classifier that was devised based on microarray data (FIGS. 5A-5C). Two microRNAs were used in each node. The correlation between the log 2(ratio) of each such pair was checked in the microarray results and the inverted $C_t$ difference between the two microRNAs in the PCR results. The correlation between the ratio of hsa-miR-221 (SEQ ID NO: 25) and hsa-miR-210 (SEQ ID NO: 20) in the two platforms was 0.92; the correlation between the ratio of hsa-miR-126 (SEQ ID NO: 41) and hsa-miR-31 (SEQ ID NO: 4) in the two platforms was 0.9 and the correlation between the ratio of hsa-miR-139-5p (SEQ ID NO: 14) and hsa-miR-200c (SEQ ID NO: 34) in the two platforms was 0.81.

The performance of the qRT-PCR classifier was checked on the 32 samples using Leave One Out Cross Validation (LOOCV). In each node, a logistic regression classifier was used. The accuracy of the qRT-PCR classifier was 90.6%, and the sensitivity per histological type was: chromophobe—100%; Oncocytoma—100%; Clear cell carcinoma—88% and papillary (chromaphil) tumors—75%.

TABLE 11

Sequences used in RT-PCR validation

| miR-name | miR SEQ ID NO: | hairpin SEQ ID NO: | MGB sequence | MGB SEQ ID NO: | FWD sequence | FWD SEQ ID NO: |
|---|---|---|---|---|---|---|
| hsa-miR-31 | 4 | 5 | CCGTTTTTTTTTTTCAGCTATG | 76 | CAGTCATTTGGGGGCAAGATGCTGGCAT | 82 |
| hsa-miR-126 | 41 | 42 | CCGTTTTTTTTTTTCGCATTAT | 77 | CAGTCATTTGGGTCGTACCGTGAGTAAT | 83 |
| hsa-miR-139-5p | 14 | 15 | CCGTTTTTTTTTTTCTGGAGAC | 78 | CAGTCATTTGGCTCTACAGTGCACGTGT | 84 |
| hsa-miR-210 | 20 | 21 | CGTTTTTTTTTTTCAGCCGCT | 79 | CAGTCATTTGGGCTGTGCGTGTGACAGC | 85 |
| hsa-miR-200c | 34 | 35 | CGTTTTTTTTTTTCCATCATT | 80 | CAGTCATTTGGGTAATACTGCCGGGTAA | 86 |
| hsa-miR-221 | 25 | 13 | CGTTTTTTTTTTTGAAACCCA | 81 | CAGTCATTTGGGAGCTACATTGTCTGCT | 87 |
| Reverse primer | 90 | | GCGAGCACAGAATTAATACGAC | | | |
| U6 | | | AATATGGAACGCTTCACG | 88 | GCAAGGATGACACGCAAATTC | 89 |

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. A method for classifying a kidney tumor sample obtained from a human subject as oncocytoma, clear cell renal cell carcinoma (RCC), papillary RCC, or chromophobe RCC, the method comprising:
   (a) obtaining a kidney tumor sample from the human subject;
   (b) determining by real-time PCR (RT-PCR) an expression profile of SEQ ID NOS: 1, 4, 6, 8, 10, 12, 14, 16, 18, 20, 22, 24-26, 28, 30, 32, 34, 36, 38, 41, 45, 47, 48, 56, 58, 60, 62, and 66 in the sample, wherein said RT-PCR comprises contacting the sample with forward and reverse primers, wherein each forward primer comprises at least 15-21 nucleotides identical to one of SEQ ID NOS: 1, 4, 6, 8, 10, 12, 14, 16, 18, 20, 22, 24-26, 28, 30, 32, 34, 36, 38, 41, 45, 47, 48, 56, 58, 60, 62, and 66, and wherein the forward primer comprising at least 15-21 nucleotides identical to SEQ ID NO: 14 comprises the sequence of SEQ ID NO: 84;
   (c) comparing said expression profile to one or more reference values; and
   (d) classifying the kidney tumor sample as oncocytoma, clear cell RCC, papillary RCC, or chromophobe RCC based on the expression profile of SEQ ID NOS: 1, 4, 6, 8, 10, 12, 14, 16, 18, 20, 22, 24-26, 28, 30, 32, 34, 36, 38, 41, 45, 47, 48, 56, 58, 60, 62, and 66 in the sample relative to the reference value, wherein:
      an increase in the expression of SEQ ID NOS: 12, 14, 18, 25, 26, 28, 30, 36, 38, 41, 48, and 66 in the sample relative to the reference value is indicative of the presence of oncocytoma;
      an increase in the expression of SEQ ID NOS: 32, 34, 36, 56, 58, 60, and 62 in the sample relative to the reference value is indicative of the presence of chromophobe RCC;
      an increase in the expression of SEQ ID NOS: 1, 6, 16, 20, 22, 24, and 41 in the sample relative to the reference value is indicative of the presence of clear cell RCC; and
      an increase in the expression of SEQ ID NOS: 4, 8, 10, 45, and 47 in the sample relative to the reference value is indicative of the presence of papillary RCC.

2. The method of claim 1, wherein the kidney tumor sample is a fresh, frozen, fixed, wax embedded or formalin fixed paraffin-embedded (FFPE) tissue sample.

3. The method of claim 1, wherein the RT-PCR method further comprises hybridization with a probe.

4. The method of claim 3, wherein the probe comprises any one of SEQ ID NOS: 76-81.

5. The method of claim 1, wherein the forward primers comprise at least one of SEQ ID NO: 82 for determining the expression profile of SEQ ID NO: 4; SEQ ID NO: 83 for determining the expression profile of SEQ ID NO: 41; SEQ ID NO: 85 for determining the expression profile of SEQ ID NO: 20; SEQ ID NO: 86 for determining the expression profile of SEQ ID NO: 34; and SEQ ID NO: 87 for determining the expression profile of SEQ ID NO: 25.

6. The method of claim 5, wherein the reverse primer comprises the sequence of SEQ ID NO: 90.

* * * * *

SEQUENCE LISTING

<160> NUMBER OF SEQ ID NOS: 90

<210> SEQ ID NO 1
<211> LENGTH: 22
<212> TYPE: RNA
<213> ORGANISM: Homo sapiense

<400> SEQUENCE: 1
uguaacagca acuccaugug ga                                          22

<210> SEQ ID NO 2
<211> LENGTH: 85
<212> TYPE: RNA
<213> ORGANISM: Homo sapiense

<400> SEQUENCE: 2
augguguuau caaguguaac agcaacucca uguggacugu guaccaauuu ccagggaga   60 ugcuguuacu uuugauggu accaa                                        85

```
<210> SEQ ID NO 3
<211> LENGTH: 85
<212> TYPE: RNA
<213> ORGANISM: Homo sapiense

<400> SEQUENCE: 3
ugguucccgc ccccuguaac agcaacucca uguggaagug cccacugguu ccaggggggc    60
ugcuguuauc uggggcgagg gccag                                         85

<210> SEQ ID NO 4
<211> LENGTH: 21
<212> TYPE: RNA
<213> ORGANISM: Homo sapiense

<400> SEQUENCE: 4
aggcaagaug cuggcauagc u                                             21

<210> SEQ ID NO 5
<211> LENGTH: 71
<212> TYPE: RNA
<213> ORGANISM: Homo sapiense

<400> SEQUENCE: 5
ggagaggagg caagaugcug gcauagcugu ugaacuggga accugcuaug ccaacauauu    60
gccaucuuuc c                                                        71

<210> SEQ ID NO 6
<211> LENGTH: 21
<212> TYPE: RNA
<213> ORGANISM: Homo sapiense

<400> SEQUENCE: 6
cugaccuaug aauugacagc c                                             21

<210> SEQ ID NO 7
<211> LENGTH: 110
<212> TYPE: RNA
<213> ORGANISM: Homo sapiense

<400> SEQUENCE: 7
gccgagaccg agugcacagg gcucugaccu augaauugac agccagugcu cucgucuccc    60
cucuggcugc caauuccaua ggucacaggu auguucgccu caaugccagc              110

<210> SEQ ID NO 8
<211> LENGTH: 22
<212> TYPE: RNA
<213> ORGANISM: Homo sapiense

<400> SEQUENCE: 8
uucccuuugu cauccuaugc cu                                            22

<210> SEQ ID NO 9
<211> LENGTH: 110
<212> TYPE: RNA
<213> ORGANISM: Homo sapiense

<400> SEQUENCE: 9
ggcuacaguc uuucuucaug ugacucgugg acuucccuuu gucauccuau gccgagaau    60 auaugaagga ggcugggaag gcaaagggac guucaauugu caucacuggc              110
```

```
<210> SEQ ID NO 10
<211> LENGTH: 21
<212> TYPE: RNA
<213> ORGANISM: Homo sapiense

<400> SEQUENCE: 10
caacaccagu cgaugggcug u                                              21

<210> SEQ ID NO 11
<211> LENGTH: 72
<212> TYPE: RNA
<213> ORGANISM: Homo sapiense

<400> SEQUENCE: 11
ugucggguag cuuaucagac ugauguugac uguugaaucu cauggcaaca ccagucgaug     60
ggcugucuga ca                                                        72

<210> SEQ ID NO 12
<211> LENGTH: 22
<212> TYPE: RNA
<213> ORGANISM: Homo sapiense

<400> SEQUENCE: 12
accuggcaua caauguagau uu                                             22

<210> SEQ ID NO 13
<211> LENGTH: 110
<212> TYPE: RNA
<213> ORGANISM: Homo sapiense

<400> SEQUENCE: 13
ugaacaucca ggucggggc augaaccugg cauacaaugu agauuucugu guucguuagg      60
caacagcuac auugucugcu ggguuucagg cuaccuggaa acauguucuc                110

<210> SEQ ID NO 14
<211> LENGTH: 22
<212> TYPE: RNA
<213> ORGANISM: Homo sapiense

<400> SEQUENCE: 14
ucuacagugc acgucucc ag                                               22

<210> SEQ ID NO 15
<211> LENGTH: 68
<212> TYPE: RNA
<213> ORGANISM: Homo sapiense

<400> SEQUENCE: 15
guguauucua cagugcacgu gucccagug uggcucggag gcuggagacg cggcccuguu      60
ggaguaac                                                             68

<210> SEQ ID NO 16
<211> LENGTH: 22
<212> TYPE: RNA
<213> ORGANISM: Homo sapiense

<400> SEQUENCE: 16
ugagaacuga auuccauagg cu                                             22
```

```
<210> SEQ ID NO 17
<211> LENGTH: 73
<212> TYPE: RNA
<213> ORGANISM: Homo sapiense

<400> SEQUENCE: 17
ccuggcacug agaacugaau uccauaggcu gugagcucua gcaaugcccu guggacucag      60
uucuggugcc cgg                                                        73

<210> SEQ ID NO 18
<211> LENGTH: 22
<212> TYPE: RNA
<213> ORGANISM: Homo sapiense

<400> SEQUENCE: 18
caaauucgua ucuaggggaa ua                                              22

<210> SEQ ID NO 19
<211> LENGTH: 110
<212> TYPE: RNA
<213> ORGANISM: Homo sapiense

<400> SEQUENCE: 19
gaucugucug ucuucuguau auacccugua gauccgaauu uguguaagga auuuguggu       60 cacaaauucg uaucuagggg aauauguagu ugacauaaac acuccgcucu                110

<210> SEQ ID NO 20
<211> LENGTH: 22
<212> TYPE: RNA
<213> ORGANISM: Homo sapiense

<400> SEQUENCE: 20
cugugcgugu gacagcggcu ga                                              22

<210> SEQ ID NO 21
<211> LENGTH: 110
<212> TYPE: RNA
<213> ORGANISM: Homo sapiense

<400> SEQUENCE: 21
acccggcagu gccuccaggc gcagggcagc cccugcccac cgcacacugc gcugcccag       60 acccacugug cgugugacag cggcugaucu gugccugggc agcgcgaccc                110

<210> SEQ ID NO 22
<211> LENGTH: 23
<212> TYPE: RNA
<213> ORGANISM: Homo sapiense

<400> SEQUENCE: 22
uuaaugcuaa ucgugauagg ggu                                             23

<210> SEQ ID NO 23
<211> LENGTH: 65
<212> TYPE: RNA
<213> ORGANISM: Homo sapiense

<400> SEQUENCE: 23
cuguuaaugc uaaucgugau aggggguuuuu gccuccaacu gacuccuaca uauuagcauu     60
aacag                                                                 65
```

```
<210> SEQ ID NO 24
<211> LENGTH: 21
<212> TYPE: RNA
<213> ORGANISM: Homo sapiense

<400> SEQUENCE: 24
gcaguccaug ggcauauaca c                                              21

<210> SEQ ID NO 25
<211> LENGTH: 23
<212> TYPE: RNA
<213> ORGANISM: Homo sapiense

<400> SEQUENCE: 25
agcuacauug ucugcuggu uuc                                             23

<210> SEQ ID NO 26
<211> LENGTH: 21
<212> TYPE: RNA
<213> ORGANISM: Homo sapiense

<400> SEQUENCE: 26
agcuacaucu ggcuacuggg u                                              21

<210> SEQ ID NO 27
<211> LENGTH: 110
<212> TYPE: RNA
<213> ORGANISM: Homo sapiense

<400> SEQUENCE: 27
gcugcuggaa gguguaggua cccucaaugg cucaguagcc aguguagauc cugucuuucg    60
uaaucagcag cuacaucugg cuacuggguc ucgauggca ucuucuagcu               110

<210> SEQ ID NO 28
<211> LENGTH: 22
<212> TYPE: RNA
<213> ORGANISM: Homo sapiense

<400> SEQUENCE: 28
cagugguuuu acccuauggu ag                                             22

<210> SEQ ID NO 29
<211> LENGTH: 100
<212> TYPE: RNA
<213> ORGANISM: Homo sapiense

<400> SEQUENCE: 29 ugucucuc ucuguguccu gccaguгgguu uacccuaug guagguuacg ucaugcuguu      60
cuaccacagg guagaaccac ggacaggaua ccggggcacc                         100

<210> SEQ ID NO 30
<211> LENGTH: 21
<212> TYPE: RNA
<213> ORGANISM: Homo sapiense

<400> SEQUENCE: 30
gcgacccaua cuuggguuca g                                              21

<210> SEQ ID NO 31
<211> LENGTH: 96
<212> TYPE: RNA
<213> ORGANISM: Homo sapiense
```

```
<400> SEQUENCE: 31
agaugugcuc uccuggccca ugaaaucaag cgugggugag accuggugca gaacgggaag    60
gcgacccaua cuugguuuca gaggcuguga gaauaa                              96

<210> SEQ ID NO 32
<211> LENGTH: 22
<212> TYPE: RNA
<213> ORGANISM: Homo sapiense

<400> SEQUENCE: 32
uaacacuguc ugguaaagau gg                                             22

<210> SEQ ID NO 33
<211> LENGTH: 95
<212> TYPE: RNA
<213> ORGANISM: Homo sapiense

<400> SEQUENCE: 33
cggccggccc uggguccauc uuccaguaca guguuggaug gucuaauugu gaagcuccua    60
acacugucug guaaagaugg cucccggug gguuc                                95

<210> SEQ ID NO 34
<211> LENGTH: 23
<212> TYPE: RNA
<213> ORGANISM: Homo sapiense

<400> SEQUENCE: 34
uaauacugcc ggguaaugau gga                                            23

<210> SEQ ID NO 35
<211> LENGTH: 68
<212> TYPE: RNA
<213> ORGANISM: Homo sapiense

<400> SEQUENCE: 35
cccucgucuu acccagcagu guuuggugc gguuggagu cucuaauacu gccggguaau      60
gauggagg                                                             68

<210> SEQ ID NO 36
<211> LENGTH: 24
<212> TYPE: RNA
<213> ORGANISM: Homo sapiense

<400> SEQUENCE: 36
uuuggcaaug guagaacuca cacu                                           24

<210> SEQ ID NO 37
<211> LENGTH: 110
<212> TYPE: RNA
<213> ORGANISM: Homo sapiense

<400> SEQUENCE: 37
gagcugcuug ccucccccg uuuuuggcaa ugguagaacu cacacuggug agguaacagg     60 auccggguggu ucuagacuug ccaacuaugg ggcgaggacu cagccggcac              110

<210> SEQ ID NO 38
<211> LENGTH: 21
<212> TYPE: RNA
<213> ORGANISM: Homo sapiense
```

```
<400> SEQUENCE: 38
uagggugcuu agcuguuaac u                                            21

<210> SEQ ID NO 39
<211> LENGTH: 108
<212> TYPE: RNA
<213> ORGANISM: Homo sapiense

<400> SEQUENCE: 39
guagauugaa gccaguugau uagggugcuu agcuguuaac uaaguguuug uggguuaag    60 ucccauuggu cuaguaaggg cuuagcuuaa uuaaaguggc ugauuugc                108

<210> SEQ ID NO 40
<211> LENGTH: 115
<212> TYPE: RNA
<213> ORGANISM: Homo sapiense

<400> SEQUENCE: 40
gaaguagauu gaagccaguu gauuaggug cuuagcuguu aacuaagugu uuguggguuu    60
aagucccauu ggucuaguaa gggcuuagcu uauuaaagu ggcugauuug cguuc         115

<210> SEQ ID NO 41
<211> LENGTH: 22
<212> TYPE: RNA
<213> ORGANISM: Homo sapiense

<400> SEQUENCE: 41
ucguaccgug aguaauaaug cg                                           22

<210> SEQ ID NO 42
<211> LENGTH: 85
<212> TYPE: RNA
<213> ORGANISM: Homo sapiense

<400> SEQUENCE: 42
cgcuggcgac gggacauuau uacuuuuggu acgcgcugug acacuucaaa cucguaccgu   60
gaguaauaau gcgccgucca cggca                                         85

<210> SEQ ID NO 43
<211> LENGTH: 22
<212> TYPE: RNA
<213> ORGANISM: Homo sapiense

<400> SEQUENCE: 43
ucgugucuug uguugcagcc gg                                           22

<210> SEQ ID NO 44
<211> LENGTH: 109
<212> TYPE: RNA
<213> ORGANISM: Homo sapiense

<400> SEQUENCE: 44
ggucgggcuc accaugacac agugugagac cucgggcuac aacacaggac ccgggcgcug   60 cucugaccccc ucgugucuug uguugcagcc ggagggacgc agguccgca              109

<210> SEQ ID NO 45
<211> LENGTH: 22
<212> TYPE: RNA
<213> ORGANISM: Homo sapiense
```

```
<400> SEQUENCE: 45
ugagaacuga auccaugggg uu                                              22

<210> SEQ ID NO 46
<211> LENGTH: 99
<212> TYPE: RNA
<213> ORGANISM: Homo sapiense

<400> SEQUENCE: 46
ccgaugugua uccucagcuu ugagaacuga auccaugggg uugucagu gucagaccuc       60 ugaaauucag uucuucagcu gggauaucuc ugucaucgu                            99

<210> SEQ ID NO 47
<211> LENGTH: 22
<212> TYPE: RNA
<213> ORGANISM: Homo Sapiense

<400> SEQUENCE: 47
uagcuuauca gacugauguu ga                                              22

<210> SEQ ID NO 48
<211> LENGTH: 23
<212> TYPE: RNA
<213> ORGANISM: Homo Sapiense

<400> SEQUENCE: 48
uacccuguag auccgaauuu gug                                             23

<210> SEQ ID NO 49
<211> LENGTH: 96
<212> TYPE: RNA
<213> ORGANISM: Homo sapiense

<400> SEQUENCE: 49
ucccuggcgu gaggguaugu gccuuuggac uacaucgugg aagccagcac caugcagucc     60
augggcauau acacuugccu caaggccuau gucauc                               96

<210> SEQ ID NO 50
<211> LENGTH: 23
<212> TYPE: RNA
<213> ORGANISM: Homo Sapiens

<400> SEQUENCE: 50
agcugguguu gugaaucagg ccg                                             23

<210> SEQ ID NO 51
<211> LENGTH: 99
<212> TYPE: RNA
<213> ORGANISM: Homo Sapiens

<400> SEQUENCE: 51
cccuggcaug guggugggg gcagcuggug uugugaauca ggccguugcc aaucagagaa      60
cggcuacuuc acaacaccag ggccacacca cacuacagg                            99

<210> SEQ ID NO 52
<211> LENGTH: 22
<212> TYPE: RNA
<213> ORGANISM: Homo Sapiense

<400> SEQUENCE: 52
cugguacagg ccuggggggac ag                                             22
```

```
<210> SEQ ID NO 53
<211> LENGTH: 84
<212> TYPE: RNA
<213> ORGANISM: Homo Sapiens

<400> SEQUENCE: 53
cuccccaugg cccugucucc caacccuugu accagugcug ggcucagacc cugguacagg    60 ccuggggac agggaccugg ggac                                           84

<210> SEQ ID NO 54
<211> LENGTH: 22
<212> TYPE: RNA
<213> ORGANISM: Homo sapiense

<400> SEQUENCE: 54
uaauacugcc ugguaaugau ga                                            22

<210> SEQ ID NO 55
<211> LENGTH: 95
<212> TYPE: RNA
<213> ORGANISM: Homo sapiense

<400> SEQUENCE: 55
ccagcucggg cagccguggc caucuuacug ggcagcauug gauggaguca ggucucuaau    60
acugccuggu aaugaugacg gcggagcccu gcacg                              95

<210> SEQ ID NO 56
<211> LENGTH: 24
<212> TYPE: RNA
<213> ORGANISM: Homo sapiense

<400> SEQUENCE: 56 acuggggcu uucgggcucu gcgu                                           24

<210> SEQ ID NO 57
<211> LENGTH: 99
<212> TYPE: RNA
<213> ORGANISM: Homo sapiense

<400> SEQUENCE: 57
uggcuaaggu guuggcucgg gcuccccacu gcaguuaccc uccccucggc guuacugagc    60 acuggggcu uucgggcucu gcgucugcac agauacuuc                           99

<210> SEQ ID NO 58
<211> LENGTH: 22
<212> TYPE: RNA
<213> ORGANISM: Homo sapiense

<400> SEQUENCE: 58
acucaaaaug ggggcgcuuu cc                                            22

<210> SEQ ID NO 59
<211> LENGTH: 69
<212> TYPE: RNA
<213> ORGANISM: Homo sapiense

<400> SEQUENCE: 59
gggauacuca aaauggggc gcuuccuuu uugucuguac ugggaagugc uucgauuuug     60
ggguguccc                                                           69
```

```
<210> SEQ ID NO 60
<211> LENGTH: 20
<212> TYPE: RNA
<213> ORGANISM: Homo sapiense

<400> SEQUENCE: 60
acucaaacug uggggggcacu                                              20

<210> SEQ ID NO 61
<211> LENGTH: 67
<212> TYPE: RNA
<213> ORGANISM: Homo sapiense

<400> SEQUENCE: 61
guggcacuca aacugugggg gcacuuucug cucucuggug aaagugccgc caucuuuga    60 guguuac                                                             67

<210> SEQ ID NO 62
<211> LENGTH: 23
<212> TYPE: RNA
<213> ORGANISM: Homo sapiense

<400> SEQUENCE: 62
guuugcacgg gugggccuug ucu                                           23

<210> SEQ ID NO 63
<211> LENGTH: 98
<212> TYPE: RNA
<213> ORGANISM: Homo sapiense

<400> SEQUENCE: 63
agaaugggca aaugaacagu aaauuuggag gccuggggcc cucccugcug cuggagaagu   60
guuugcacgg gugggccuug ucuuugaaag gaggugga                           98

<210> SEQ ID NO 64
<211> LENGTH: 22
<212> TYPE: RNA
<213> ORGANISM: Homo sapiense

<400> SEQUENCE: 64
aacuggcccu caaaguccccg cu                                           22

<210> SEQ ID NO 65
<211> LENGTH: 83
<212> TYPE: RNA
<213> ORGANISM: Homo sapiense

<400> SEQUENCE: 65
guggucucag aaucggggu uugagggcga gaugaguuua uguuuuaucc aacuggcccu    60 caaaguccccg cuuuuggggu cau                                          83

<210> SEQ ID NO 66
<211> LENGTH: 22
<212> TYPE: RNA
<213> ORGANISM: Homo sapiense

<400> SEQUENCE: 66
uaaugccccu aaaaauccuu au                                            22
```

```
<210> SEQ ID NO 67
<211> LENGTH: 111
<212> TYPE: RNA
<213> ORGANISM: Homo sapiense

<400> SEQUENCE: 67
agaguguuca aggacagcaa gaaaaaugag ggacuuucag gggcagcugu guuuucugac        60 ucagcauaa ugccccuaaa aauccuuauu guucuugcag gugcaucgg g                 111

<210> SEQ ID NO 68
<211> LENGTH: 22
<212> TYPE: RNA
<213> ORGANISM: Homo sapiense

<400> SEQUENCE: 68
uguaaacauc cuacacucag cu                                                22

<210> SEQ ID NO 69
<211> LENGTH: 88
<212> TYPE: RNA
<213> ORGANISM: Homo sapiense

<400> SEQUENCE: 69
accaaguuuc aguucaugua aacauccuac acucagcugu aauacaugga uuggcuggga        60
gguggauguu uacuucagcu gacuugga                                          88

<210> SEQ ID NO 70
<211> LENGTH: 22
<212> TYPE: RNA
<213> ORGANISM: Homo sapiense

<400> SEQUENCE: 70
uagguaguuu ccuguuguug gg                                                22

<210> SEQ ID NO 71
<211> LENGTH: 84
<212> TYPE: RNA
<213> ORGANISM: Homo sapiense

<400> SEQUENCE: 71
acuggucggu gauuuaggua guuuccuguu guugggaucc accuuucucu cgacagcacg        60
acacugccuu cauuacuuca guug                                              84

<210> SEQ ID NO 72
<211> LENGTH: 22
<212> TYPE: RNA
<213> ORGANISM: Homo sapiense

<400> SEQUENCE: 72
uaacacuguc ugguaacgau gu                                                22

<210> SEQ ID NO 73
<211> LENGTH: 90
<212> TYPE: RNA
<213> ORGANISM: Homo sapiense

<400> SEQUENCE: 73 ccgggcccu gugagcaucu uaccggacag ugcuggauuu cccagcuuga cucuaacacu        60
gucugguaac gauguucaaa ggugacccgc                                        90
```

```
<210> SEQ ID NO 74
<211> LENGTH: 22
<212> TYPE: RNA
<213> ORGANISM: Homo sapiense

<400> SEQUENCE: 74
aagacgggag gaaagaaggg ag                                              22

<210> SEQ ID NO 75
<211> LENGTH: 76
<212> TYPE: RNA
<213> ORGANISM: Homo sapiense

<400> SEQUENCE: 75
gagggggaag acgggaggaa agaagggagu gguuccauca cgccuccuca cuccucuccu     60
cccgucuucu ccucuc                                                    76

<210> SEQ ID NO 76
<211> LENGTH: 23
<212> TYPE: DNA
<213> ORGANISM: Artificial sequence
<220> FEATURE:
<223> OTHER INFORMATION: Synthetic

<400> SEQUENCE: 76
ccgttttttt tttttcagct atg                                            23

<210> SEQ ID NO 77
<211> LENGTH: 23
<212> TYPE: DNA
<213> ORGANISM: Artificial sequence
<220> FEATURE:
<223> OTHER INFORMATION: Synthetic

<400> SEQUENCE: 77
ccgttttttt tttttcgcat tat                                            23

<210> SEQ ID NO 78
<211> LENGTH: 23
<212> TYPE: DNA
<213> ORGANISM: Artificial sequence
<220> FEATURE:
<223> OTHER INFORMATION: Synthetic

<400> SEQUENCE: 78
ccgttttttt tttttctgga gac                                            23

<210> SEQ ID NO 79
<211> LENGTH: 22
<212> TYPE: DNA
<213> ORGANISM: Artificial sequence
<220> FEATURE:
<223> OTHER INFORMATION: Synthetic

<400> SEQUENCE: 79 cgttttttttt ttttcagccg ct                                            22

<210> SEQ ID NO 80
<211> LENGTH: 22
<212> TYPE: DNA
<213> ORGANISM: Artificial sequence
<220> FEATURE:
<223> OTHER INFORMATION: Synthetic
```

```
<400> SEQUENCE: 80
cgtttttttt ttttccatca tt                                              22

<210> SEQ ID NO 81
<211> LENGTH: 22
<212> TYPE: DNA
<213> ORGANISM: Artificial sequence
<220> FEATURE:
<223> OTHER INFORMATION: Synthetic

<400> SEQUENCE: 81
cgtttttttt ttttgaaacc ca                                              22

<210> SEQ ID NO 82
<211> LENGTH: 28
<212> TYPE: DNA
<213> ORGANISM: Artificial sequence
<220> FEATURE:
<223> OTHER INFORMATION: Synthetic

<400> SEQUENCE: 82
cagtcatttg ggggcaagat gctggcat                                        28

<210> SEQ ID NO 83
<211> LENGTH: 28
<212> TYPE: DNA
<213> ORGANISM: Artificial sequence
<220> FEATURE:
<223> OTHER INFORMATION: Synthetic

<400> SEQUENCE: 83
cagtcatttg ggtcgtaccg tgagtaat                                        28

<210> SEQ ID NO 84
<211> LENGTH: 28
<212> TYPE: DNA
<213> ORGANISM: Artificial sequence
<220> FEATURE:
<223> OTHER INFORMATION: Synthetic

<400> SEQUENCE: 84
cagtcatttg gctctacagt gcacgtgt                                        28

<210> SEQ ID NO 85
<211> LENGTH: 28
<212> TYPE: DNA
<213> ORGANISM: Artificial sequence
<220> FEATURE:
<223> OTHER INFORMATION: Synthetic

<400> SEQUENCE: 85
cagtcatttg ggctgtgcgt gtgacagc                                        28

<210> SEQ ID NO 86
<211> LENGTH: 28
<212> TYPE: DNA
<213> ORGANISM: Artificial sequence
<220> FEATURE:
<223> OTHER INFORMATION: Synthetic

<400> SEQUENCE: 86
cagtcatttg ggtaatactg ccgggtaa                                        28
```

```
<210> SEQ ID NO 87
<211> LENGTH: 28
<212> TYPE: DNA
<213> ORGANISM: Artificial sequence
<220> FEATURE:
<223> OTHER INFORMATION: Synthetic

<400> SEQUENCE: 87
cagtcatttg ggagctacat tgtctgct                                   28

<210> SEQ ID NO 88
<211> LENGTH: 18
<212> TYPE: DNA
<213> ORGANISM: Artificial sequence
<220> FEATURE:
<223> OTHER INFORMATION: Synthetic

<400> SEQUENCE: 88
aatatggaac gcttcacg                                              18

<210> SEQ ID NO 89
<211> LENGTH: 21
<212> TYPE: DNA
<213> ORGANISM: Artificial sequence
<220> FEATURE:
<223> OTHER INFORMATION: Synthetic

<400> SEQUENCE: 89
gcaaggatga cacgcaaatt c                                          21

<210> SEQ ID NO 90
<211> LENGTH: 22
<212> TYPE: DNA
<213> ORGANISM: artificial sequence
<220> FEATURE:
<223> OTHER INFORMATION: Synthetic

<400> SEQUENCE: 90
gcgagcacag aattaatacg ac                                         22
```